(12) United States Patent
Kim et al.

(10) Patent No.: US 11,679,099 B2
(45) Date of Patent: Jun. 20, 2023

(54) USE OF HIF-2α INHIBITORS FOR TREATING CHONDROSARCOMA, OR PREVENTING RECURRENCE AND METASTASIS THEREOF

(71) Applicant: SEOUL NATIONAL UNIVERSITY R&DB FOUNDATION, Seoul (KR)

(72) Inventors: Jin-Hong Kim, Seoul (KR); Hyeonkyeong Kim, Seoul (KR); Hyeon-Seop Kim, Seoul (KR); Yongsik Cho, Seoul (KR)

(73) Assignee: SEOUL NATIONAL UNIVERSITY R&DB FOUNDATION, Seoul (KR)

(*) Notice: Subject to any disclaimer, the term of this patent is extended or adjusted under 35 U.S.C. 154(b) by 24 days.

(21) Appl. No.: 15/930,799

(22) Filed: May 13, 2020

(65) Prior Publication Data

US 2021/0353599 A1  Nov. 18, 2021

(51) Int. Cl.

| | |
|---|---|
| C07D 471/04 | (2006.01) |
| A01N 43/90 | (2006.01) |
| A61K 31/4245 | (2006.01) |
| A61K 31/277 | (2006.01) |
| A61P 35/04 | (2006.01) |
| A61K 31/704 | (2006.01) |
| C12N 15/113 | (2010.01) |
| A61K 33/243 | (2019.01) |

(52) U.S. Cl.
CPC ........ *A61K 31/4245* (2013.01); *A61K 31/277* (2013.01); *A61K 31/704* (2013.01); *A61K 33/243* (2019.01); *A61P 35/04* (2018.01); *C12N 15/1136* (2013.01)

(58) Field of Classification Search
CPC .............. A61K 31/4245; A61K 31/277; A61K 31/704; A61K 33/243; A61P 35/04; C12N 15/1136; C12N 2310/14; C12N 15/113
See application file for complete search history.

(56) References Cited

U.S. PATENT DOCUMENTS 9,173,946 B2 * 11/2015 Egorov ...................... A61P 3/14
2018/0140569 A1 * 5/2018 Josey ...................... A61K 45/06

FOREIGN PATENT DOCUMENTS

KR  10-2011-0127943 A   11/2011
WO  2009/020119 A1   2/2009

OTHER PUBLICATIONS

Johnson, J. I., et al. "Relationships between drug activity in NCI preclinical in vitro and in vivo models and early clinical trials." British journal of cancer 84.10 (2001): 1424-1431. (Year: 2001).*
Gura, Trisha. "Systems for identifying new drugs are often faulty." (1997): 1041-1042. (Year: 1997).*
Freshney, R. Ian. "Culture of animal cells: a manual of basic technique." 1983. (Year: 1983).*
Dermer, Gerald B. "Another anniversary for the war on cancer." Bio/technology 12.3 (1994): 320-320. (Year: 1994).*
Grimer et al. European Journal of Cancer 43 (2007) 2060-2065. (Year: 2007).*
Yoshimoto et al. Child's Nerv Syst (1995) 11:250-253 (Year: 1995).*
Scheuermann, Thomas H., et al. "Allosteric inhibition of hypoxia inducible factor-2 with small molecules." Nature chemical biology 9.4 (2013): 271-276. (Year: 2013).*
Schmidt, Robert E., and Drury R. Reavill. "Metastatic chondrosarcoma in a corn snake (*Pantherophis guttatus*)." Journal of Herpetological Medicine and Surgery 22.3-4 (2012): 67-69. (Year: 2012).*
Chen et al., "Association of Elevated HIF-2alpha Levels with Low Beclin 1 Expression and Poor Prognosis in Patients with Chondrosarcoma", Ann Surg Oncol, 2011, vol. 18, pp. 2364-2372.
Chen et al., "Recombinant human PDCD5 sensitizes chondrosarcomas to cisplatin chemotherapy in vitro and in vivo", Apoptosis, 2010, vol. 15, 805-813.
Yu et al., "Development of Inhibitors Targeting Hypoxia-Inducible Factor 1 and 2 for Cancer Therapy", Yonsei Med J, 2017, vol. 58, No. 3, pp. 489-496.
Gelderblom et al., "The Clinical Approach Towards Chondrosarcoma", The Oncologist, 2008, vol. 13, pp. 320-329.
Jung, "Human Tumor Xenograft Models for Preclinical Assessment of Anticancer Drug Development", Toxicol. Res., 2014, vol. 30, No. 1, pp. 1-5.
Liao et al., "Current advances in animal model of chondrosarcoma and related research (Review)", Biomedical Reports, 2013, vol. 1, pp. 3-6.
Ordonez et al., "The Clinical Relevance of Molecular Genetics in Soft Tissue Sarcomas", Adv Anat Pathol, 2010, vol. 17, pp. 162-181.
Roell et al., "An Introduction to Terminology and Methodology of Chemical Synergy—Perspectives from Across Disciplines", Frontiers in Pharmacology, 2017, vol. 8, Article 158, 11 pages.
Staffa et al., "Synergy in Nanomedicine: What it is Not, and What it Might Be", Nano Lett., 2021, vol. 21, pp. 5457-5460.
Shen, "Cancer biomarkers and targeted therapies", Cell & Bioscience, 2013, vol. 3, Issue 6, 2 pages.
Ting-Chao Chou, "Drug combination studies and their synergy quantification using the Chou-Talalay method", Cancer Research, Jan. 15, 2010, 70(2), pp. 440-446, doi: 10.1158/0008-5472.
Hyeonkyeong KIM et al., "A system-level approach identifies HIF-2α as a critical regulator of chondrosarcoma progression", Nature Communications, 2020, vol. 11, Article 5023 pp. 1-16, https://doi.org/10.1038/s41467-020-18817-7.
Simone Leaderer et al, "Additive Dose Response Models: Defining Synergy", Frontiers in Pharmacology, Nov. 2019, vol. 10, Article 1384, doi: 10.3389/fphar.2019.01384.

* cited by examiner

*Primary Examiner* — Mina Haghighatian
*Assistant Examiner* — Janice Y Silverman
(74) *Attorney, Agent, or Firm* — The PL Law Group. PLLC

(57) ABSTRACT

The present disclosure relates a method of treating chondrosarcoma or suppressing metastasis or recurrence thereof by regulating HIF-2α. The present method can be effectively used for treating chondrosarcoma or suppressing metastasis or recurrence thereof by inhibiting HIF-2α during the development and metastasis of chondrosarcoma, particularly dedifferentiated chondrosarcoma.

2 Claims, 66 Drawing Sheets

Specification includes a Sequence Listing.

USE OF HIF-2α INHIBITORS FOR TREATING CHONDROSARCOMA, OR PREVENTING RECURRENCE AND METASTASIS THEREOF

BACKGROUND OF THE INVENTION

Sequence Listing

The Sequence Listing submitted in text format (.txt) filed on May 13, 2020, named "SequenceListing.txt", created on May 6, 2020 (5.61 KB), is incorporated herein by reference.

Field of the Invention

The present disclosure relates to methods of for treating chondrosarcoma, or preventing recurrence and metastasis thereof using HIF-2α inhibitors.

Description of the Related Art

Chondrosarcomas are common primary neoplasms arising within the bone, constituting one-third of skeletal system cancers. Chondrosarcomas is the third most frequent cancers of bone-soft tissue, and the most frequent cancer of bone-soft tissue found in adult. The incidence rate per 100,000 people for bone-soft tissue cancer is 0.9, and the survival rate for 5 years is about 67.7%. The 10-year survival rate of malignant chondrosarcoma is 29% and the recurrence rate is 13%. The most common treatment for chondrosarcoma is surgical removal, followed by chemotherapy and radiotherapy after surgery. However, for chemotherapy and radiotherapy, the extracellular matrix is thick, so there is resistance to radiotherapy. In general, anticancer drugs such as doxorubicin and cisplatin, which are commonly used, are not delivered effectively, so it is difficult to expect a full anticancer effect through anticancer drugs, as well as other side effects, making the effective therapy of chondrosarcomas difficult.

There is also no treatment specific for chondrosarcoma. Currently, metastasis occurs in 70% of patients with stage 3 chondrosarcomas, and recurrence occurs in 13% of patients. Thus lowering the incidence of recurrence and metastasis of cartilage cancer remains a major challenge in the field.

Korea Patent Application Publication No. 2011-0127943 relates to suppressing the expression of HIF-2α (hypoxia-inducible factor-2α) gene and discloses a pharmaceutical composition comprising substance inhibiting HIF-2α activity for treating arthritis.

Therefore, there is a urgent need to develop an anticancer agent that can effectively suppresses chondrosarcoma, recurrence and metastasis thereof.

SUMMARY OF THE INVENTION

The present disclosure is to provide a method and composition for treating, suppressing metastasis or recurrence of chondrosarcoma by regulating HIF-2α activity or its expression.

In one aspect, there is provided a method of treating chondrosarcoma, suppressing metastasis or recurrence thereof in a subject in need thereof comprising the step of administering to the subject an effective amount of an inhibitor of HIF-2α.

In one embodiment, the inhibitor of HIF-2α is an agent that inhibit the transcriptional activity of the HIF-2α.

In other embodiment, the inhibitor of HIF-2α is TC-S7009 [N-(3-Chloro-5-fluorophenyl)-4-nitro-2,1,3-benzoxadiazol-5-amine], or its derivative PT2385 [((S)-3-((2,2-difluoro-1-hydroxy-7-(methylsulfonyl)-2,3-dihydro-1H-inden-4-yl)oxy)-5-fluorobenzonitrile)], or its derivative PT2399 [((S)-3-((7-((difluoromethyl)sulfonyl)-2,2-difluoro-1-hydroxy-2,3-dihydro-1H-inden-4-yl)oxy)-5-luorobenzonitrile).

In still other embodiment, the chondrosarcoma is a dedifferentiated chondrosarcoma.

In still other embodiment, the method further comprising the step of administering to the subject an effective amount of chemotherapeutic agent.

In still other embodiment, HIF-2α inhibitor is TC-S7009, PT2385 or PT2399, and the chemotherapeutic agent is cisplatin or doxorubicin.

In still other embodiment, HIF-2α inhibitor is an agent that inhibit the expression of HIF-2α gene to its mRNA, or the expression of HIF-2α gene to its protein such as siRNA which degrade the transcribed mRNA to prevent from it to be translated into proteins. For example, such siRNA is represented by SEQ ID Nos: 3 and 4, which has complementary sequence to form dsRNA.

In other aspect, there is provided a method of determining the prognosis of chondrosarcoma by analyzing CNA of EPAS1 loci.

The present disclosure relates a method of treating chondrosarcoma or suppressing metastasis or recurrence thereof by regulating HIF-2α. The present method can be effectively used for treating chondrosarcoma or suppressing metastasis or recurrence thereof by inhibiting HIF-2α during the development and metastasis of chondrosarcoma, particularly dedifferentiated chondrosarcoma.

BRIEF DESCRIPTION OF THE DRAWINGS

FIG. 1A is the results showing that three gene modules, M1, M2, and M3 were identified by WGCNA using transcriptome data of patients with chondrosarcoma (GSE12475). Cancer-promoting (CP) annotations significantly associated with each module were analyzed using IPA. For each module, the top 10 CP annotations were arranged in order of P-value and plotted with the activation z-score. $-\log_{10}$(P-value)>2 was used as the cutoff.

FIG. 1B is the results showing that the predicted upstream regulators of the M1 module were color-coded according to the sum of the activation z-scores of the linked nodes (Left). Representative CP annotations regulated by HIF-2α were arranged in order of the activation z-score (Right).

FIG. 1C is the results of the experiment in which GSEA was performed with the M1 module geneset using transcriptome data obtained from chondrocytes infected with Ad(adenovirus)-Epas1 compared to those infected with Ad-Ctrl (GSE73659). NES, normalized enrichment score.

FIG. 1D is the results showing that Network connections of M1 module genes visualized by VisANT. The hub genes are located toward the center of the network. Target genes of HIF-2α was determined based on the HIF-2α overexpressed transcriptome data set (GSE73659) in chondrocytes.

FIGS. 1E to 1G represent Histology and IHC analysis of cartilage and chondrosarcoma biopsies.

FIG. 1E is the results showing representative images of H&E, Safranin-O staining, and IHC against HIF-2α in normal articular cartilage, well differentiated chondrosarcoma and dedifferentiated chondrosarcoma sample. Scale bar=50 μm.

FIG. 1F is the results showing quantification of HIF-2α expression in well-differentiated chondrosarcoma (n=45) and dedifferentiated chondrosarcoma (n=20) scored by Hirsch index (H-index) (P<0.001)

FIG. 1G is the results of the experiments in which the staining intensity against HIF-2α was graded to three different categories. The percentages of samples in each category among well-differentiated and dedifferentiated chondrosarcomas are presented as pie graph. Fisher's exact test was performed to measure statistical significance of the two groups of chondrosarcomas (P<0.001).

FIG. 1H is the results of the experiments in which patients were grouped by conducting k-means clustering based on values of the principal component axis that represents the HIF-2α activation state. The clinical data of the patients in groups 1 and 2 is summarized in Table 1. (Scale bar, 50 μm.) Values indicate the mean±SEM, Student's t test. Error bars are ±SEM, and the two-sided Student's t test was used to generate P values; M=module; WGCNA=weighted gene co-expression network analysis; CP=cancer-promoting; IPA=ingenuity pathway analysis; GSEA=geneset enrichment analysis; NES=normalized enrichment score; P=P value; Ad=adenovirus; Ctrl=control; H&E=hematoxylin and eosin; IHC=immunohistochemistry; yr=year; OS=overall survival.

FIG. 2A is a schematic representation of the chondrosarcoma orthotopic mouse model (Top). (Bottom) Primary chondrosarcoma tumors formed within the tibial intramedullary canal following SW1353 xenograft. EP, epiphyseal plate (Bottom) stained with safranin-O/hematoxylin. Scale Bar=100 μm.

FIG. 2B is the results showing histology and IHC analysis of primary and pulmonary metastatic chondrosarcoma tumors. Yellow arrowheads indicate HIF-2α positive cells. Marking Bar=25 μm FIG. 2C is the results showing IF of Lamin B, human mitochondria, and HIF-2α in primary and pulmonary metastatic tumors (Left). T, tumor; B, bone; L, lung. The percentage of HIF-2α positive cells among human mitochondria positive cells (P<0.001, n=6) (Right).

FIG. 2D is a schematic illustration of chondrosarcoma xenograft model used for the HIF-2α knockdown study.

FIG. 2E shows representative images of tibial bone xenografted with SW1353-shCtrl or SW1353-shEPAS1 cells (Left). Images were obtained by staining with safranin-O/hematoxylin. Scale Bar=50 μm. Percentage of mice bearing extraosseous outgrowth that originated from the intramedullary region of the tubular bone and invaded into surrounding muscle tissues (n=6) (Right).

FIG. 2F shows (left) Metastatic growth of chondrosarcoma cells in the lung stained with H&E, Scale Bar=50 μm. (Middle) The percentage of mice bearing lung metastases (n=6). (Right) The number of metastatic foci in the lung per animal (P=0.03, n=6). (Scale bars, 25 μm.) Values indicate the mean±SEM, *P<0.05, ***P<0.001, Student's t test. EP=epiphyseal plate; H&E=hematoxylin and eosin; IHC=immunohistochemistry; IF=immunofluorescence; T=tumor; B=bone; L=lung; shCtrl=control shRNA; shEPAS1=EPAS1 shRNA.

FIG. 3A shows a Venn diagram of differentially downregulated genes following HIF-1α or HIF-2α knockdown in SW1353 cells.

FIG. 3B is the results of GSEA performed with the M1 module geneset (FIG. 1A) using the SW1353 transcriptome following HIF-1α (Top) or HIF-2α (Bottom) knockdown FIG. 3C is the results of pathway enrichment analysis of transcriptome changes in response to HIF-2α knockdown which was conducted using the MSigDB 'hallmark' genesets (Liberzon A, Birger C, Thorvaldsdottir H, Ghandi M, Mesirov J P, Tamayo P. The Molecular Signatures Database (MSigDB) hallmark gene set collection. Cell Syst. 2015; 1(6):417-425). Each box indicates an individual hallmark geneset and is color-coded for NES value. Blue and yellow colors represent negative and positive enrichment, respectively.

FIG. 3D shows Heatmaps of the top 50 downregulated genes among epithelial mesenchymal transition geneset and the top 50 upregulated genes among apoptosis and p53 pathway genesets in SW1353 cells following HIF-2α knockdown. GSEA=geneset enrichment analysis; M=module; Ctrl=control; NES=normalized enrichment score; P=P value; MsigDB=the molecular signatures database; FC=fold change.

FIG. 4A shows (Left) representative images of crystal violet staining from the transwell invasion assay using SW1353 cells transduced with lentiviruses harboring ctrl or EPAS1 shRNA. Scale Bar=200 μm. (Right) Quantitation of invaded SW1353 (P=0.05, n=3) and OUMS-27 (P=0.005, n=4) cells in indicated conditions. The number of cells invaded was counted in random image fields and normalized to the number of cell expression ctrl shRNA.

FIG. 4B shows the results of the migration assay using SW1353 (representative images, n=3) and OUMS-27 cells (n=4) expressing indicated shRNAs. The reprehensive images of the migration assay using SW1353 cells were shown in the left panel (P=N.S.). Scale Bar=200 μm.

FIG. 4C shows the relative mRNA levels of EPAS1, MMP1, MMP2 and MMP9 measured by qRT-PCR in the indicated stable cell lines (P=0.02 (EPAS1), P=0.009 (MMP1), P=0.02 (MMP2), P=0.01 (MMP9), n=7).

FIG. 4D shows the relative total MMP activity in SW1353 cells overexpressing eGFP or HIF-2α (P<0.001, n=6).

FIG. 4E shows (Left) Gelatin degradation assay using SW1353 cells expressing ctrl or EPAS1 shRNAs. Nucleus was stained with DAPI. Scale Bar=100 μm. (Right) Quantitation of relative gelatin degradation area (P<0.001, n=4) measured with ImageJ and normalized with control area.

FIG. 4F shows GSEA with the cancer stem cell geneset using transcriptome data of SW1353 cells transfected with ctrl or EPAS1 siRNA.

FIG. 4G shows qRT-PCR analysis of EPAS1 transcript in SW1353 (Left) (P<0.001, n=9) and OUMS-27 (P=0.04, n=9) or (Right) primary chondrosarcoma cells (GSE47823; n=2), grown as a monolayer or as spheres.

FIG. 4H and FIG. 4I show the results of sphere formation assay of SW1353 and OUMS-27 cells transduced with lentiviruses harboring indicated shRNAs. Representative images and quantitative analyses of the sphere formation assay using (H) SW1353 (P=0.03, n=6) Scale Bar=200 μm; and (I) OUMS-27 cells expressing the indicated shRNAs ((P=0.02, n=5).

Error bars indicate ±SEM 0|ᴅ, two-sided Student's t test or ANOVA was used to obtain P values; N.S.=non-significant, *P<0.05, P<0.01, *P<0.001. Ctrl=control; GSEA=geneset enrichment analysis; NES=normalized enrichment score; P=P value; IPA=ingenuity pathway analysis; shCtrl=control shRNA; shEPAS1=EPAS1 shRNA.

FIG. 5A to 5L shows the pharmacological inhibition of HIF-2α potentiates anti-neoplastic effects of cisplatin in chondrosarcoma.

Figure 5A:
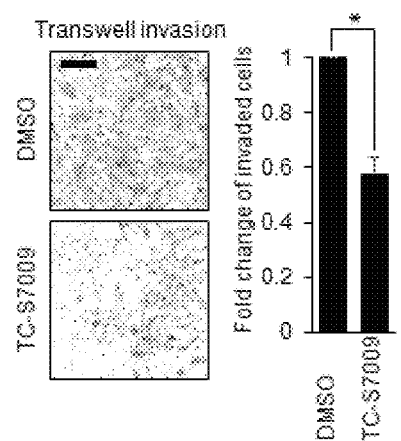

FIG. 5A is the results of Transwell invasion (n=3) assay using SW1353 cells treated with DMSO or 10 μM TC-S7009. Representative images were shown, the invaded cells were calculated on the random image fields and normalized to the cells treated with DMSO. Scale Bar=200 μm.

Figure 5B:
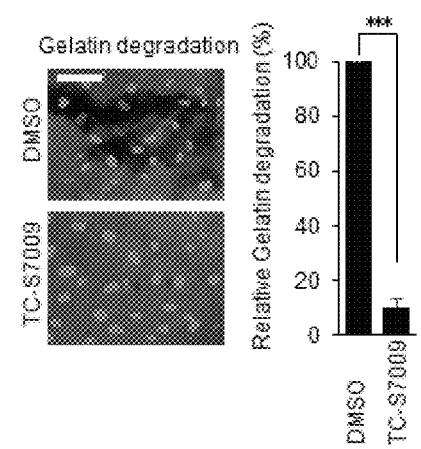

FIG. 5B shows the representative images and the relative degradation area of the gelatin degradation (P<0.001, n=3) assay using SW1353 cells treated with DMSO or 10 μM TC-S7009. Scale Bar=50 μm.

Figure 5C:
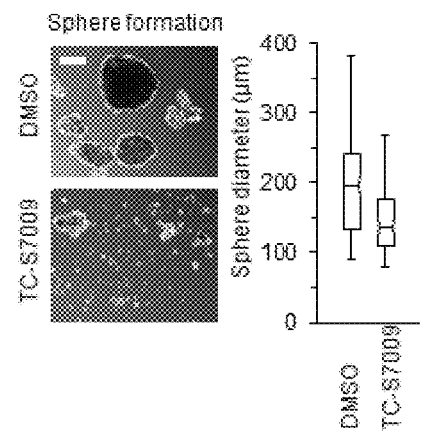

FIG. 5C is the results of sphere formation (n=3) assays using SW1353 cells treated with DMSO or 10 μM TC-S7009 assay using SW1353 cells treated with DMSO or 10 μM TC-S7009. The representative images were shown and the diameter of the spheres were measured. Box-whisker plot were used to present the data. Scale Bar=200 μm.

Figure 5D:
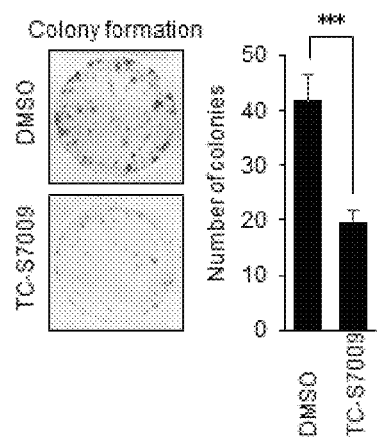

FIG. 5D is the results of colony formation (P<0.001, n=5) assays using SW1353 cells treated with DMSO or 10 μM TC-S7009 assay using SW1353 cells treated with DMSO or 10 μM TC-S7009. The representative images and quantification results were shown.

Figure 5E:
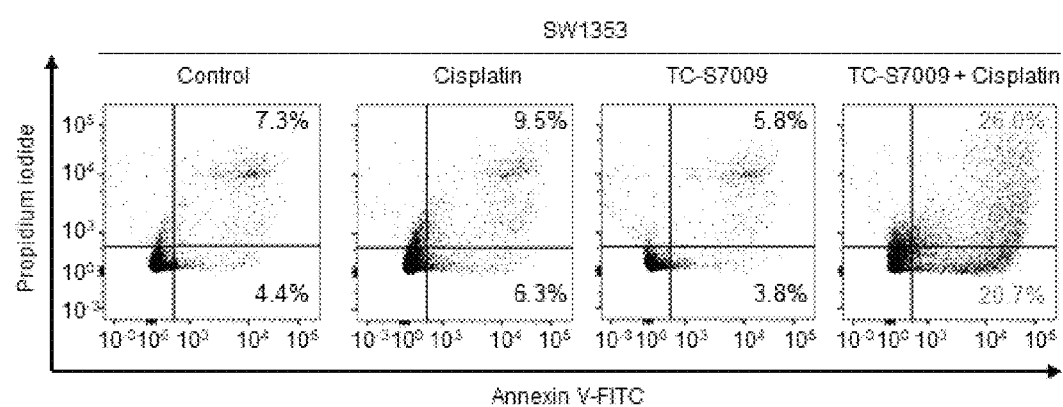

FIG. 5E shows the percentage of apoptotic cells measured by flow cytometry of SW1353 cells stained with Annexin-V and PI after treatment with vehicle, TC-S7009, cisplatin, or TC-S7009 and cisplatin in combination.

Figure 5F:
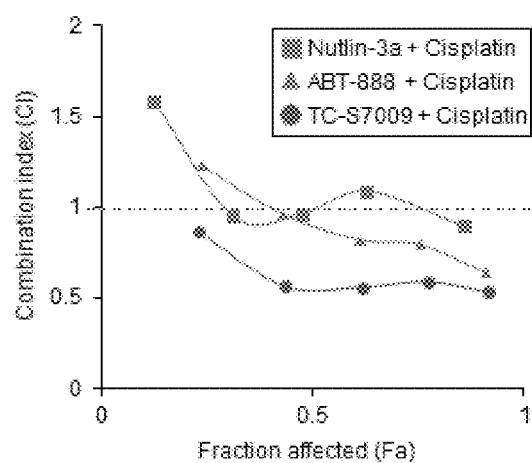

FIG. 5F shows the results of the experiments in which CI was calculated for three different combination therapies based on results obtained with MTT assay in SW1353 cells. CI scores were defined as additive (CI=1), synergistic (CI<1), and antagonistic (CI>1).

Figure 5G:
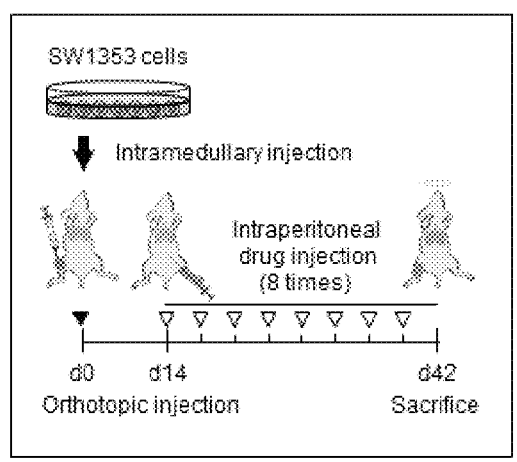

FIG. 5G is a schematic diagram of combination chemotherapy with TC-S7009. Mice were intraperitoneally injected 8 times with DMSO, cisplatin, TC-S7009, or cisplatin plus TC-S7009, twice a week from two weeks following the orthotopic xenograft (n=5).

Figure 5H:
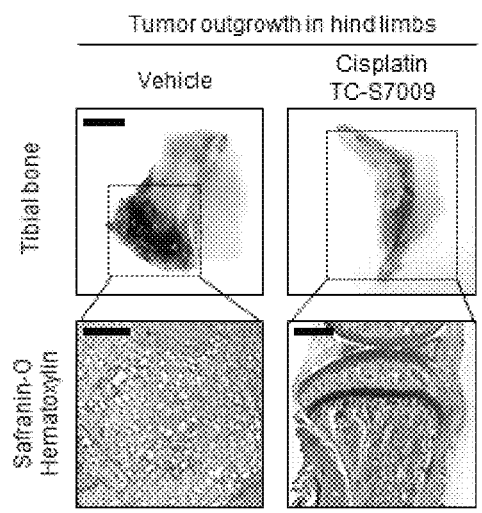

FIG. 5H shows representative macroscopic and histological images of tibial bones. The sections were stained with Safranin-O and hematoxylin. Scale Bar=50 mm (Top), 100 μm (left, bottom), 500 μm (Right, bottom).

Figure 5I:
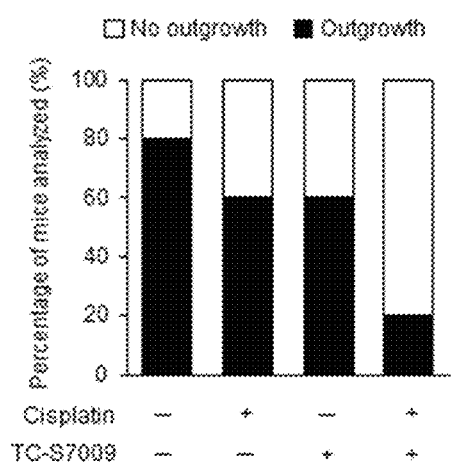

FIG. 5I shows percentage of mice bearing extraosseous outgrowth originating from the intramedullary location of tubular bone.

Figure 5J:
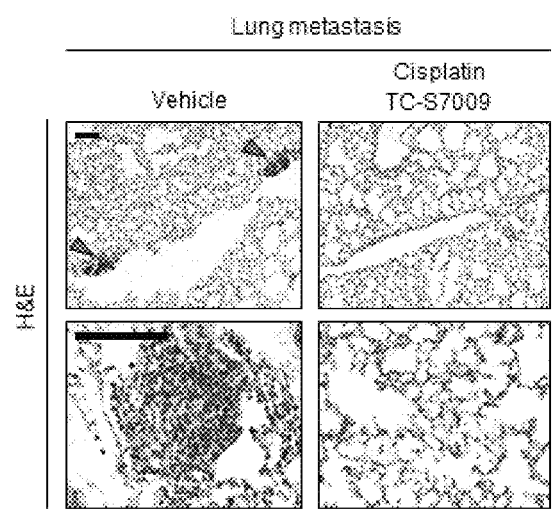

FIG. 5J shows the metastatic growth of chondrosarcoma cells in the lung. Yellow arrowheads indicate metastatic region in lung. Scale Bar=100 μm.

Figure 5K:
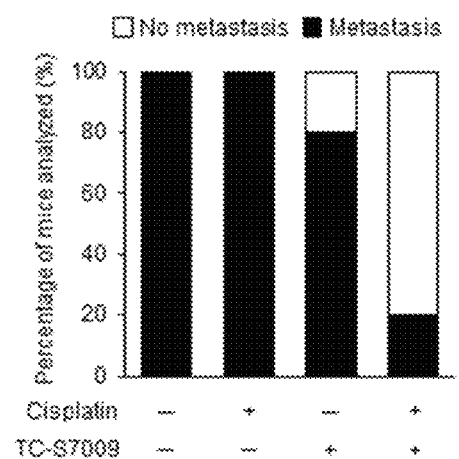

FIG. 5K shows the percentage of mice bearing lung metastases (n=5).

Figure 5L:
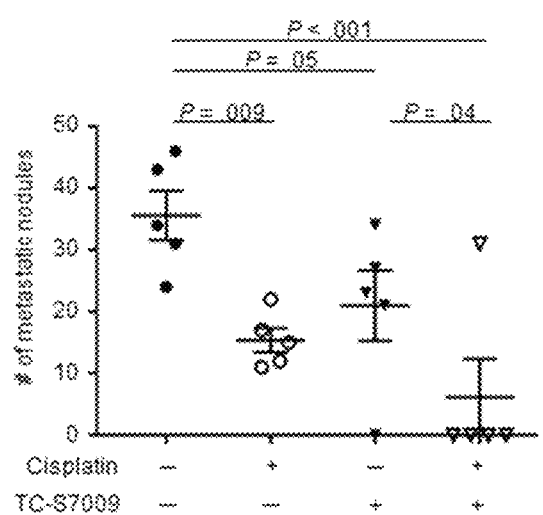

FIG. 5L shows the dot plot of the number of metastatic foci in the lung per animal (n=5).

Values indicate the mean±SEM, two-sided Student's t test or ANOVA was used for calculation of P values. *P<0.05, ***P<0.001. P=P value; CI=combination index; H&E=hematoxylin and eosin.

FIG. 6A to 6E shows that CNAs of HIF-2α pathway components are associated with chondrosarcoma patient prognosis.

Figure 6A:
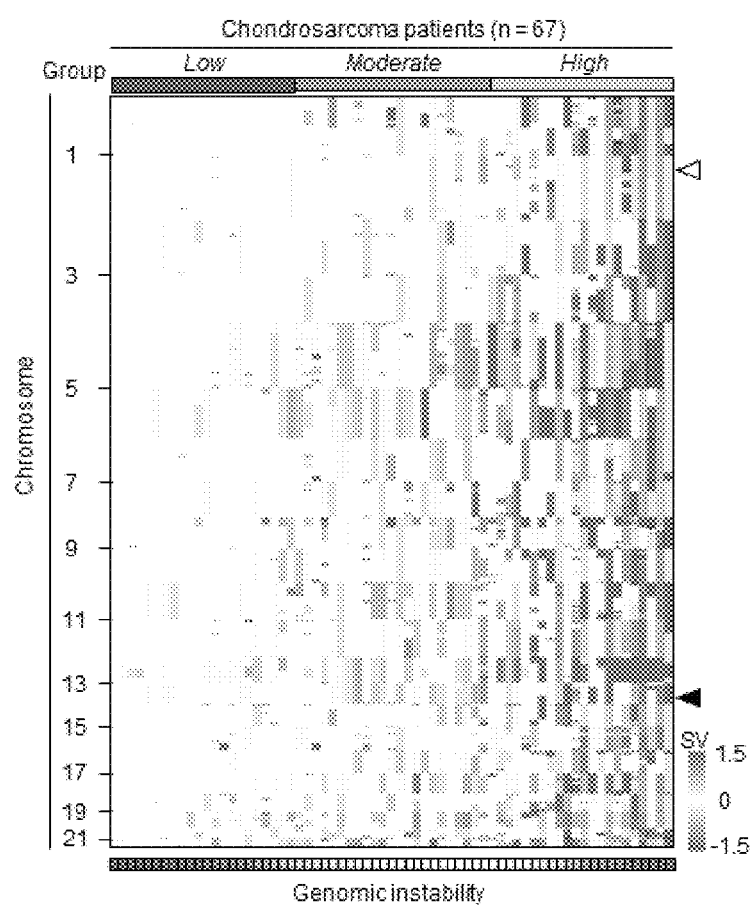

FIG. 6A shows the smoothed copy number data for 67 patients with chondrosarcoma. Patients were ordered by interchromosomal variation degree of their chondrosarcoma, a genomic instability indicator, and divided into low (n=22), moderate (n=23), and high (n=22) instability groups. Solid and open arrowheads indicate HIF1A and EPAS1 loci, respectively. CNAs: gain (red), stable (white), and loss (blue). SV, smoothing value.

Figure 6B:
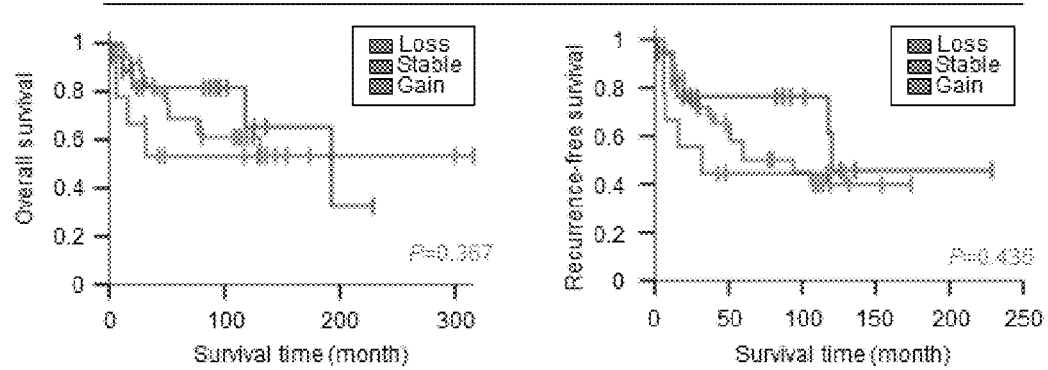
Figure 6C:
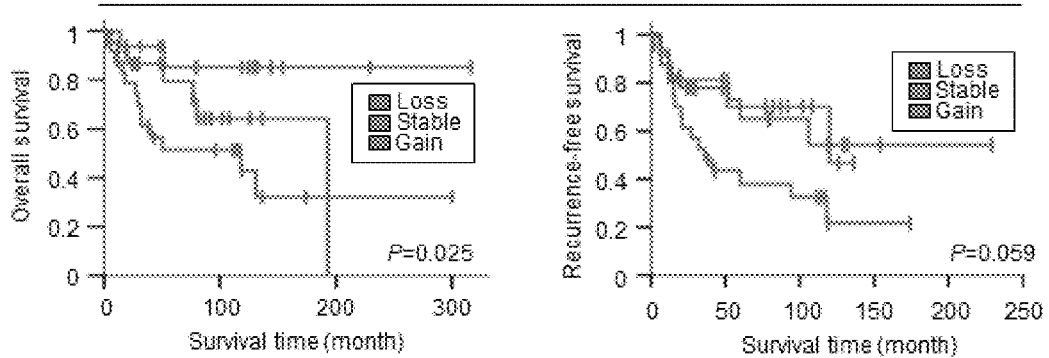

FIG. 6B and FIG. 6C show the Kaplan-Meier plot of overall and recurrence-free survival of the 67 patients stratified by copy number status of HIF1A (B) and EPAS1 (C) loci. CNA profiles were grouped by copy number status: gain (HIF1A, n=9; EPAS1, n=24), stable (HIF1A, n=18; EPAS1, n=27), and loss (HIF1A, n=37; EPAS1, n=16).

Figure 6D:
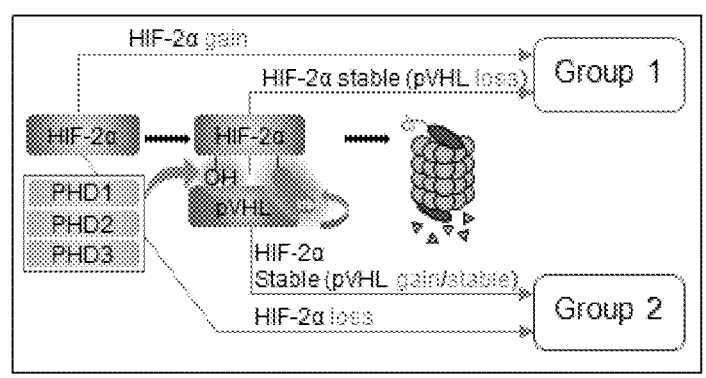

FIG. 6D is a schematic illustration of categorizing criteria of 67 patients based on the CNA status of EPAS1 and VHL loci. The patients of group I is a group expected to show over-reaction in HIF-2α pathway compared to group II patients.

Figure 6E:
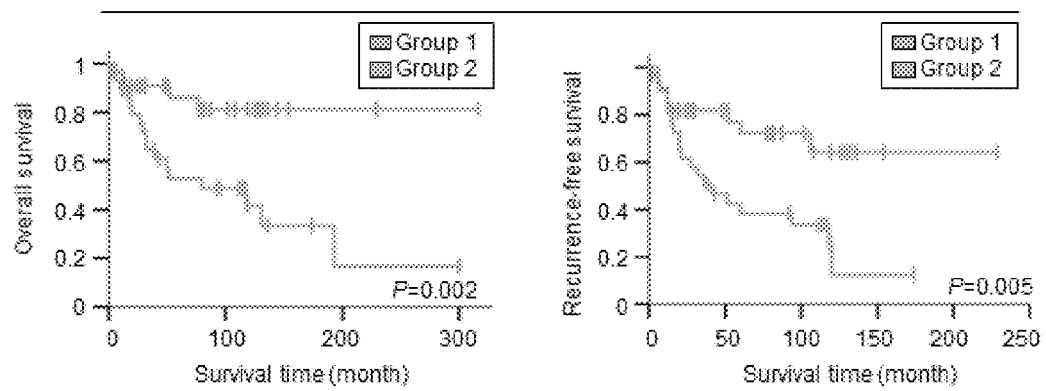

FIG. 6E shows Kaplan-Meier plot of overall and recurrence-free survival of the 67 patients stratified by group.

Statistical significance was calculated using the log-rank test. SV=smoothing value; GLAD=gain and loss analysis of DNA; CNA=copy number alteration; pVHL=von Hippel-Lindau tumor suppressor; PHD=prolyl hydroxylase domain-containing protein; P=P value.

Figure 7:
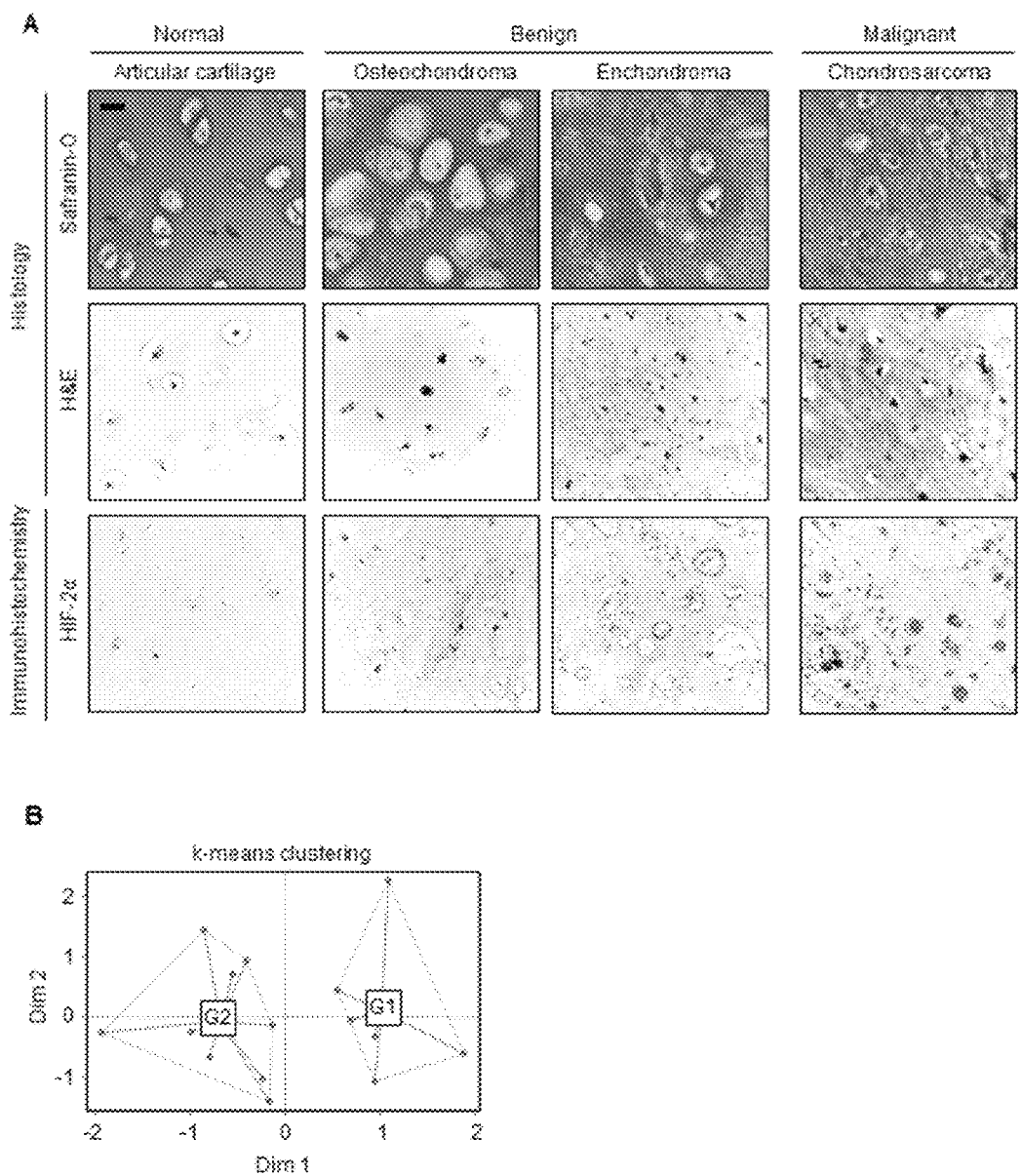

FIG. 7 shows the results of profiling of HIF-2α expression in bone and cartilage tumors. (A) Safranin-O, H&E, and IHC for HIF-2α in human normal articular cartilage, osteochondroma, enchondroma, and chondrosarcoma specimens. (A) Safranin-O, H&E, and IHC for HIF-2α in human normal articular cartilage, osteochondroma, enchondroma, and chondrosarcoma specimens. (Scale bar, 25 μm.) (B) Using chondrosarcoma transcriptome data (GSE12475), chondrosarcoma patients were grouped into two groups, G1 and G2, by conducting k-means clustering based on values of principal component axis that represented the HIF-2α activation state. HIF-2α activation state was determined based on the expression levels of HIF-2α target genes included in the M1 module. H&E=hematoxylin and eosin; IHC= immunohistochemistry; G=group; M=module; IPA=ingenuity pathway analysis; PCA=principal component analysis; Dim= dimension.

Figure 8A:
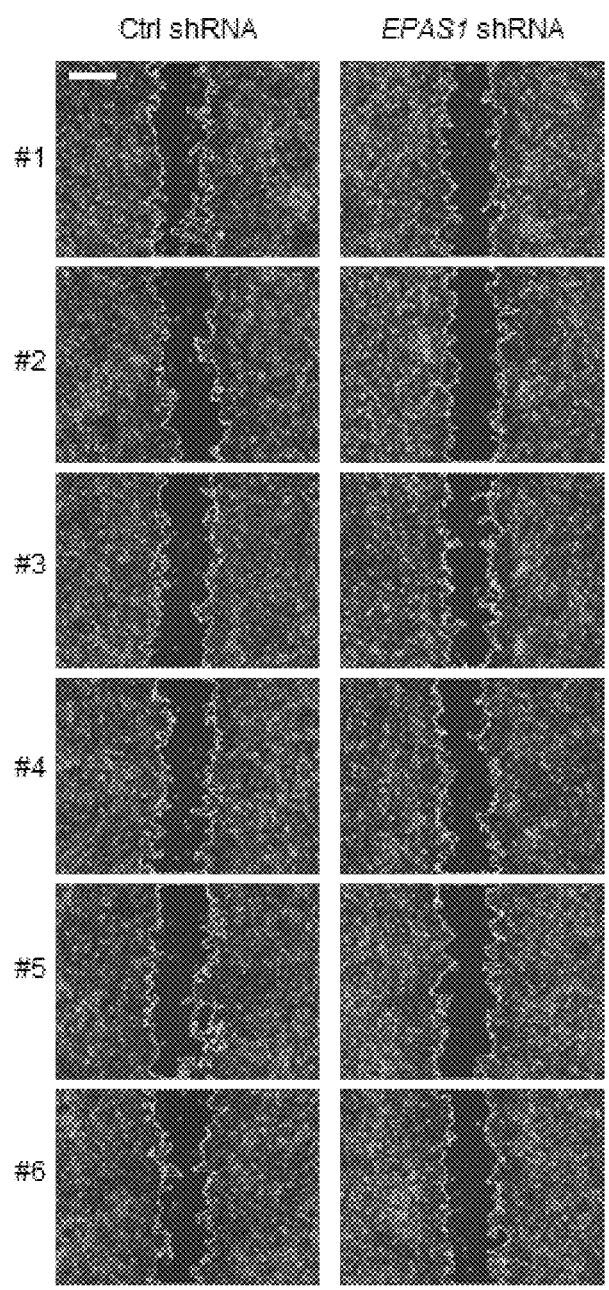
Figure 8B:
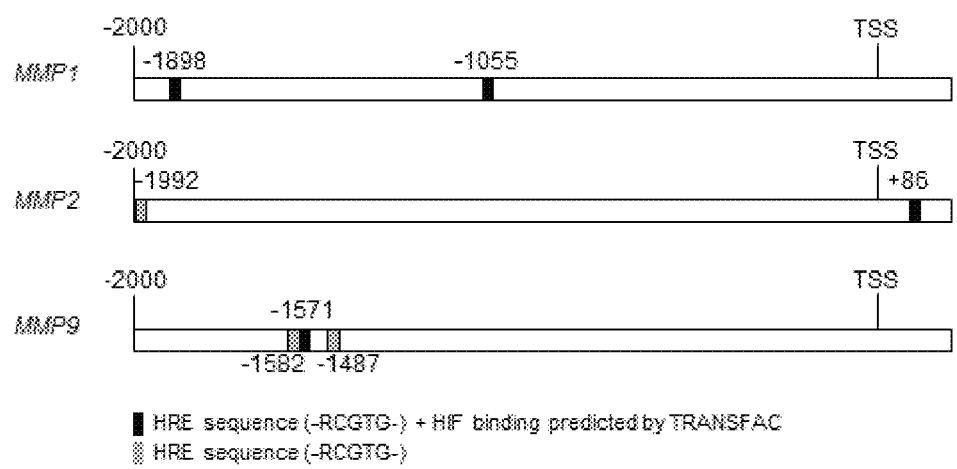
Figure 8C:
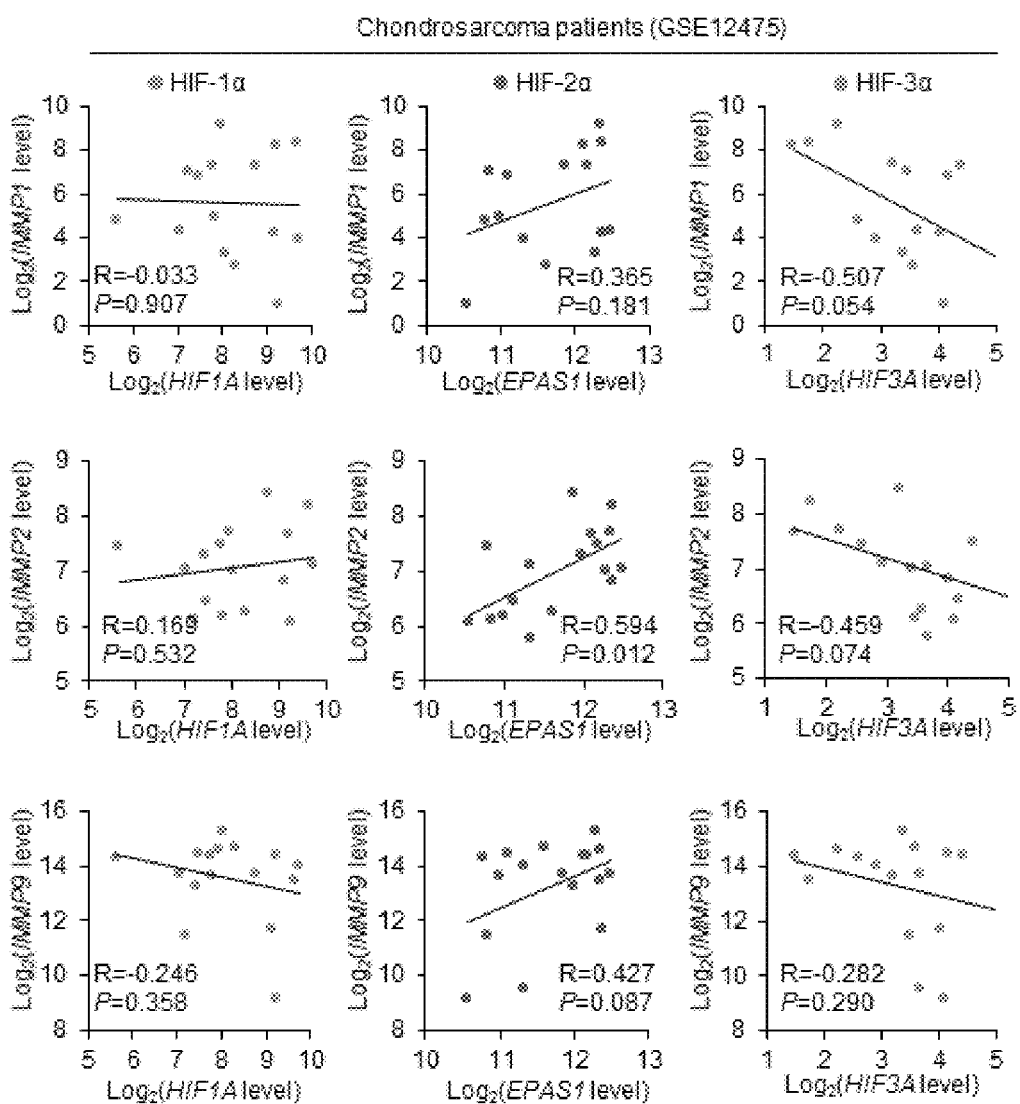

FIG. 8A to 8C show the results that HIF-2α regulates expression of matrix-degrading enzymes without affecting migratory behavior of chondrosarcoma cells. (A) Migration assay of SW1353 cells transduced with lentiviruses harboring indicated shRNAs (n=6). Representative images of cell migration are shown. Images were analyzed to quantify the migrated area using the Image-Pro Premier software. (B) The black box indicates the HRE sequence that is predicted as HIF binding site by TRANSFAC® (GeneXplain GmbH) database. The gray box indicates the site that possesses the HRE sequence on the promoter. TSS, transcription start site; HRE, hypoxia response element; TRANSFAC, TRANScription FACtor database. (C) Graph showing correlation between transcript levels of HIF family and MMP1, MMP2, and MMP9 genes in patients with chondrosarcoma (GSE12475). R and P-values were calculated based on Pearson's correlation. (Scale bar, 200 μm.) P=P value; Ctrl=control; MMP=matrix metalloproteinase; HRE= hypoxia response element; TRANSFAC=TRANScription FACtor database; HIF=hypoxia inducible factor; TSS= transcription start site.

Figure 9:
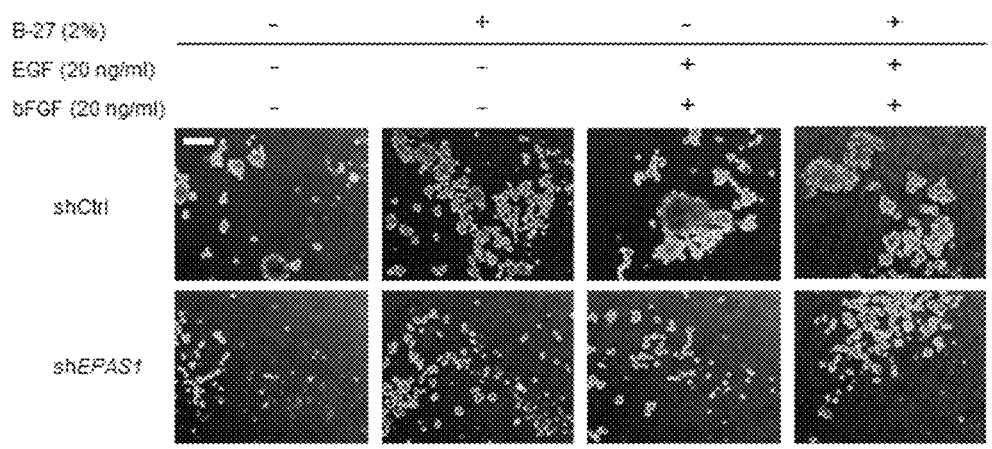
Figure 9:
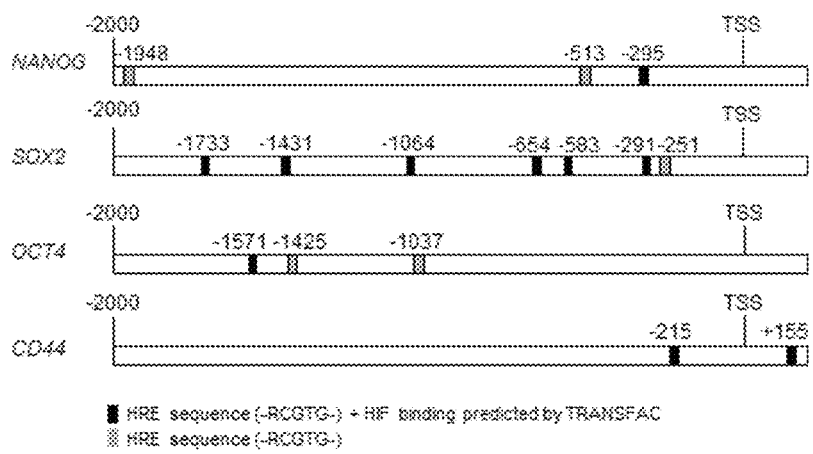

FIG. 9 shows the results that HIF-2α confers stemness of chondrosarcoma cells by enhancing expression of pluripotent factors possessing potential HIF binding sites. (A) Sphere formation assay performed with SW1353 cells transduced with lentiviruses harboring ctrl or EPAS1 shRNA. Cells were treated with or without B-27 (2%), EGF (20 ng/ml), or bFGF (20 ng/ml). Images are representative of three independent experiments. (Scale bar, 200 μm.) (B) The black box indicates the HRE sequence that is predicted as HIF binding site by TRANSFAC® (GeneXplain GmbH) database. The gray box indicates the site that possesses the HRE sequence on the promoter. EGF=epidermal growth factor; bFGF=basic fibroblast growth factor; shCtrl=control shRNA; shEPAS1=EPAS1 shRNA; HRE=hypoxia response element; TRANSFAC=TRANScription FACtor database; HIF=hypoxia inducible factor; TSS=transcription start site.

FIG. 10A to 10I shows the results that HIF-2α overexpression promotes metastatic behaviors of chondrosarcoma cells in cell culture and xenograft models. (A, Top) Representative phase-contrast images of SW1353 stable cell lines overexpressing eGFP or HIF-2α. (Scale bar, 150 μm.) (Bottom) Relative expression level of EPAS1 in the stable cell lines. (B, Left) Representative images of crystal violet staining from the transwell invasion assay using SW1353 cells overexpressing eGFP or HIF-2α. (Scale bar, 200 μm.) (Right) Invaded cells were counted in random image fields and normalized relative to the control (n=5). (C) Migration assay was performed using SW1353 cells transduced with indicated lentiviruses harboring eGFP or HIF-2α. (Scale bar, 100 μm) Images were taken 0 and 24 h after wound formation (Left), and the migrated area was measured 12 h after wound formation (Right, n=6). (D) Sphere formation assay of SW1353 cells overexpressing eGFP or HIF-2α. Representative images are shown, and the number and the diameter of spheres were measured. (Scale bar, 200 μm.) Cells were grown in serum-free media (n=6). A box-and-whisker plot was used to represent the data. (E) Quantification of the colony formation assay of SW1353 cells transduced with indicated lentiviruses. Colonies were counted after crystal violet staining (Right), and representative images are presented (Left, n=9). (F) Schematic illustration of the chondrosarcoma xenograft model used in the HIF-2α overexpression study. SW1353 cells (1×10$^5$ cells per mouse) overexpressing eGFP or HIF-2α were orthotopically injected into athymic mice and analyzed after seven weeks. (G) Metastatic growth of chondrosarcoma cells in the lung examined by H&E staining. (Scale bar, 200 μm.) (H) The number of mice bearing lung metastases was counted and plotted by their percentage (n=6, eGFP #1; 5, eGFP #2; 6, EPAS1 #1; 4, EPAS1 #2). (1) The number of metastatic foci in the lung per animal was counted and plotted using dot plot (n=6, eGFP #1; 5, eGFP #2; 6, EPAS1 #1; 4, EPAS1 #2). Values indicate the mean±SEM, *P<0.05, N.S., not significant, Student's t test (B-E) and ANOVA (1). The two-sided Student's t test or ANOVA was used to generate P values; N.S.=non-significant, *P<0.05. P=P value; HIF=hypoxia inducible factor; H&E=hematoxylin and eosin.

FIG. 11A to 11D shows the results that the HIF-2α inhibitor TC-S7009 effectively blocks transcriptional activity and tumor-initiating potential of HIF-2α without affecting cell viability and migration ability. (A) SW1353 cells were co-transfected with pcDNA3 or pcDNA3-EPAS1 and the HRE containing reporter plasmid in the absence or presence of different doses of TC-S7009. HRE reporter activity was normalized to Renilla luciferase activity (n=5). (B) Trypan blue exclusion assay to test the effect of TC-S7009 on cell viability of SW1353 cells (n=3). (C) Colony formation assay of SW1353 cells in the absence or presence of different doses of TC-S7009. The number of colonies counted using the ImageJ software (n=5). (D) Migration assay performed using SW1353 cells treated with DMSO or 10 μM TC-S7009. Representative images are shown (Left), and the relative area of migration (Right) was determined using the Image-Pro Premier software (n=6). (Scale bar, 200 μm.) Values indicate the mean±SEM, *P<0.001, N.S., not significant, ANOVA (A-C) and Student's t test (D). P values; N.S.=non-significant, *P<0.001. HRE=hypoxia response element; P=P value.

Figure 12:
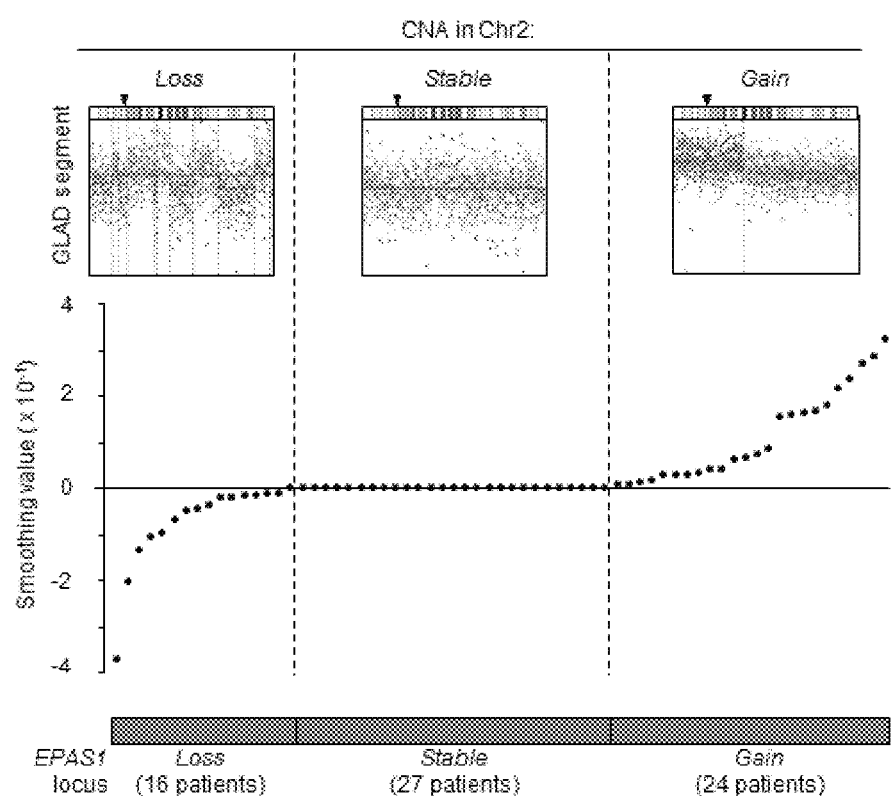

FIG. 12 is the results showing CNA profiling of EPAS1 locus on chromosome 2. CNA profiles of 67 chondrosarcoma patients were ordered and grouped into three groups by EPAS1 copy number status: loss (green, n=16), stable (yellow, n=27), and gain (red, n=24). Inlets are representative genomic profiles for chromosome 2 of patients containing loss, stable, or gain of copy number in the EPAS1 locus. Arrowheads indicate the EPAS1 position in chromosome 2. Vertical dashed red lines in inlet images represent the breakpoints detected with GLAD; the assigned statuses are indicated by a color code. Chr2, chromosome 2.

DETAILED DESCRIPTION OF THE EMBODIMENTS

The present disclosure is in part based on the discovery that HIF-2α is a key factor in the development, metastasis and recurrence of chondrosarcomas particularly dedifferentiated chondrosarcomas. Specifically, it was identified herein that HIF-2α as a transcription factor of a gene module causing malignant dedifferentiated chondrosarcomas conferred chondrosarcoma cells invasiveness and tumor-initiating capacity. In a mouse model, it was identified herein that the inhibition of HIF-2α effectively suppressed extraosseous outgrowth and metastasis to lung of chondrosarcoma. In addition, it was identified herein that the combined use of conventional chemotherapeutic agent and HIF-2α inhibitor exerted a synergistic apoptotic effect on chondrosarcoma cells and thus eliminating malignant chondrosarcomas. Also, it was found here that CNA (Copy Number Alteration) of EPAS1 (HIF-2α) gene is closely related with poor prognosis.

Accordingly, in one aspect, the present disclosure relates to a method of treating chondrosarcoma, suppressing metastasis or recurrence thereof by regulating HIF-2α in cells, wherein the regulation of HIF-2α includes regulation of the expression of HIF-2α gene to mRNAs, expression of HIF-2α mRNA into proteins, and/or activity, i.e., its activity as a transcription factor, c of HIF-2α proteins.

In one embodiment, the method is for treating chondrosarcoma, suppressing metastasis or recurrence thereof in a subject in need thereof comprising the step of administering to the subject an effective amount of an inhibitor of HIF-2α.

HIF (Hypoxia Induced Factor)-1α and HIF-2α are a factor that mainly drives the response of cells to hypoxia, the expression of which is increased under hypoxic condition. HIF-1α increases the influx of glucose through GLUT1 expression and induces the proliferation of cancer cells by inducing blood vessels through VEGF expression increasing thus increasing the glucose supply to the cancer cells. The Warburg effect, a specific metabolic process of cancer cells, is regulated by HIF-1α and produces a material essential for cell proliferation by promoting rapid energy supply through anaerobic respiration and biosynthesis of amino acids, fats, and nucleic acids. HIF-2α binds to the promoters of the genes downstream of the HIF-2α pathway and regulates the transcription of these genes into transcripts and also is known to be involved in cartilage matrix breakdown by promoting the expression of enzymes such as MMP in arthritis. However, HIF-2α's involvement in the development, metastasis and recurrence of chondrosarcoma, particularly dedifferentiated chondrosarcoma is not known.

Chondrosarcoma is a malignant tumor that forms cartilage, the second most common bone tumor after osteosarcoma, and accounts for 10-20% of primary malignant bone tumors. It is found most frequently in the pelvis and occurs also in the femur, humerus, and ribs. The type is divided into a primary chondrosarcoma that occurs without anterior lesions, and a secondary chondrosarcoma caused by malignant changes of such as enchondrosarcoma or osteochondroma. In addition, it can be classified into central chondrosarcoma, which occurs inside the bone, and peripheral chondrosarcoma which occurs on the surface, depending on the site of occurrence. Histologically, it can be classified into conventional, mesenchymal, myxoid, dedifferentiated and clear cell types.

Chondrosarcoma ranges from low-grade tumors with little metastatic potential to high-grade dedifferentiated aggressive tumors characterized by metastatic metastasis and recurrence, and cannot be treated and can have a poor prognosis. Chondrosarcoma can be classified according to histological methods and is important in clinical aspects and prognosis. Malignant chondrosarcoma can be graded on a scale of 1 to 3 based on nuclear size, dyeing pattern (hyperchromasia), cell division activity and cytoplasmic extent (Chondrosarcoma of the pelvis. A review of sixty-four cases. AUPring M E, Weber K L, Unni K K, Sim F H SOJ Bone Joint Surg Am. 2001; 83-A(11):1630).

In particular, high-grade chondrosarcoma includes dedifferentiated chondrosarcoma. Dedifferentiated chondrosarcoma is a mixture of low-grade malignant hyalin carcinoma, low-grade chondrosarcoma, and high-grade dedifferentiated chondrosarcoma. High-grade dedifferentiated chondrosarcoma has a variety of features, including undifferentiated sarcoma, osteosarcoma, angiosarcoma, fibrosarcoma, rhabdomyosarcoma, smooth muscle sarcoma and giant cell tumor. Dedifferentiated chondrosarcoma is a serious malignant tumor with a very poor prognosis. The average survival time was as short as 6 months, and the patient survival rate for 5 years was as low as 10% to 13%. Very few patients survive two years after surgery (The molecular pathogenesis of dedifferentiated chondrosarcoma. Akio Sakamoto Indian J Orthop. 2014 May-June; 48(3): 262-265).

Various HIF-2α inhibitors which is able to suppress the activity of HIF-2α proteins expressed in chondrosarcoma tissues may be included in the present disclosure. The expression of HIF-2α proteins are increased in various cancers and function as a dimer form and regulate the transcription of the genes downstream of HIF-2α pathway.

In one embodiment, HIF-2α inhibitors are agents that can bind to PAS-B region present in HIF-2α structure, thus inhibiting the dimerization of HIF-2α and preventing DNA binding of HIF-2α. The inhibitor of transcriptional activity of HIF-2α is a substance capable of reducing the intracellular protein concentration of the target gene by reducing the expression thereof through inhibiting the expression of the target gene.

Thus, various substances that exhibit such effects as disclosed herein can be used as the inhibitors of the present disclosure. Substances capable of inhibiting the expression at the transcriptional and/or translational level or activity include, for example, small molecules, proteins including such as antibodies and polypeptides or nucleic acid molecules including RNA and DNA such as antisense oligonucleotides, siRNAs, shRNA or miRNA or any combinations thereof, but are not limited thereto.

The term expression, as used herein, includes all steps of the process in which a gene is made into a protein in vitro or intracellularly, including, for example, gene to mRNA transcription, mRNA to protein translation.

As used herein, "activity" refers to a biological function that allows the expressed protein to function natively in the cell.

In one embodiment according to the present disclosure, an inhibitor that may be used for the present disclosure is a substance previously known as a HIF-2α specific inhibitor. For example TC-S7009 (N-(3-Chloro-5-fluorophenyl)-4-nitro-2,1,3-benzoxadiazol-5-amine CAS No. 1422955-31-4), and its derivatives PT2385 ((S)-3-((2,2-difluoro-1-hydroxy-7-(methylsulfonyl)-2,3-dihydro-1H-inden-4-yl)oxy)-5-fluorobenzonitrile; CAS No: 1672665-49-4) and PT2399 ((S)-3-((7-((difluoromethyl)sulfonyl)-2,2-difluoro-1-hydroxy-2,3-dihydro-1H-inden-4-yl)oxy)-5-fluorobenzonitrile; CAS No: 1672662-14-4) is used. They act specifically on HIF-2α, inhibiting its dimerization and DNA binding, ultimately inhibiting its transcriptional activity. For the first time it was identified herein that these substances inhibit the growth and metastasis of malignant chondrosarcoma, particularly dedifferentiated chondrosarcoma.

In other embodiment, HIF-2α inhibitors are antibodies that can specifically recognize HIF-2α proteins and inhibit, interfering or suppressing the activity and/or action of HIF-2α. The term antibody as used herein is intended to include whole antibodies, antigen-binding fragments thereof, and antibodies or fragments functionally equivalent thereto. In addition, the antibody of the present invention may be of IgG, IgM, IgD, IgE, IgA or IgY type, and may be of IgG1, IgG2, IgG3, IgG4, IgA1 or IgA2 class or subclass thereof. Antibodies of the invention include monoclonal, polyclonal, chimeric, single chain, bispecific, anthropogenic and humanized antibodies, and active fragments and antibody mimetics thereof.

In other embodiment, HIF-2α inhibitors are polypeptides that can interfere and or inhibit HIF-2α expression, activity and/or action/mechanism. The term polypeptide as used herein refers to a polymer of natural or synthetic amino acids, and does not refer to a specific length as long as it has the function as disclosed herein, and includes peptides and oligopeptides. Such polypeptides include natural or artificially modified ones, such as glycosylated, acetylated, phosphorylated, and the like.

In other embodiments, the inhibitors that may be included in the present disclosure are nucleotides, such as small interfering RNA (siRNA) or small hairpin RNA (shRNA) or miRNA (microRNA). The siRNA, shRNA and miRNA are silencing mRNA transcripts through RNA interference by forming RISC (RNA Induced Silencing Complex) in which siRNAs sequence specifically bind to the mRNA transcripts. siRNA, shRNA and miRNA have a sequence significantly complementary to their target sequence. The term significant complementarity means a sequence having at least about 70%, about 80%, about 90%, or about 100% complementary to at least 15 consecutive bases of a target sequence. Various antisense oligonucleotides, siRNA, shRNA and/or miRNA targeting HIF-2α gene from various sources may be used for the present disclosure as long as they bind to a target sequence to silence them. Also biological equivalent, derivatives and analogues thereof are also included. Antisense oligonucleotides are a short synthetic nucleotide known in the art, and they bind to a coding sequence of a target protein and suppress/decrease the expression level of a target protein. Antisense RNA may have an optimum length according to the methods of transfer or types of target genes and be for example 6, 8 or 10 to 40, 60 or 100 bases in length. In one embodiment, siRNA is used to suppress the expression of HIF-2α gene.

In one embodiment, sequences of such siRNAs are represented by SEQ ID Nos: 3 and 4 for sense and antisense, respectively for HIF-2α. The above sequences have complementarity and may be used as dsRNA in which a sense and antisense sequences bind to each other. Further such sequences may further comprise at its 3' terminal dTdT overhang. As described in FIG. 3, such siRNAs effectively suppress the expression of HIF-2α at the cellular level and thus decreasing the concentration of HIF-2α protein, which affected the expression of gene related to metastasis, apoptosis and p53 signaling pathway. This indicates that siRNAs can be effectively used for the suppression of growth, metastasis and survival of chondrosarcoma.

As used herein, the terms "treat," "treatment," and "treating" include alleviating, abating or ameliorating at least one symptom of a disease or condition, and/or reducing severity, progression and/or duration thereof, and/or preventing additional symptoms, and includes prophylactic and/or therapeutic measures. The disease or symptoms includes disease or symptoms that requires cartilage regeneration for effective treatment.

The present method or composition further comprises anticancer agent for chemotherapy. The pathological and cellular characteristics of chondrosarcoma, such as their low proliferation rate, have limited the therapeutic efficacy of conventional anticancer therapies. In the present disclosure, it has been demonstrated that HIF-2α inhibitor combined with existing chemotherapeutic agents effectively relieves malignant tumors of chondrosarcoma through a synergistic effect that causes cell death of chondrosarcoma cells. Thus, in the present methods and compositions, various chemotherapeutic agents for chondrosarcoma may be used in combination with HIF-2α inhibitors. In the present methods, chemotherapeutic agents are co-administered with HIF-2α inhibitors.

The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," and "patient," are used interchangeably herein and refer to any mammalian subject for whom diagnosis, treatment, or therapy is desired, particularly humans.

The term "co-administration" refers to a combination therapy by any administration route in which two or more agents are administered to cells, to a patient or to a subject. Co-administration of agents may be referred to as combination therapy or combination treatment. In regard to treatment of patients, the agents may be the same dosage formulations or separate formulations. For combination treatment with more than one active agent, where the active agents are in separate dosage formulations, the active agents can be administered concurrently, or they each can be administered at separately staggered times. The agents may be administered simultaneously or sequentially, as long as they are given in a manner sufficient to allow both agents to achieve effective concentrations in the body. The agents may be administered by different routes, e.g., one agent may be administered intravenously while a second agent is administered intramuscularly, intravenously or orally.

In one embodiment, cisplatin is used. Cisplatin functions through inhibiting the replication of DNA by binding to DNA. Thus various chemotherapeutic agents that is capable of inhibiting the replication of DNA, for example such as Doxorubicin may be used in combination with HIF-2α inhibitors. Doxorubicin is commonly used chemotherapeutic agent for treating chondrosarcoma, but it is known to have anticancer resistance in chondrosarcoma cells. In the present disclosure, it is found that the resistance to chemotherapeutic agent was improved. In one embodiment, by treating the cells with HIF-2α inhibitor, the resistance to cisplatin was improved. In other embodiment, by treating the cells with HIF-2α inhibitor, the sensitivity to cisplatin was improved. Doxorubicin and cisplatin is an anticancer agent commonly used in the treatment of chondrosarcoma, and chondrosarcoma is found to be resistant to all of these anticancer agents. In another embodiment, the inhibitor of HIF-2α according to the present disclosure may be used to improve resistance to doxorubicin. The inhibitor of HIF-2α according to the present disclosure can be used to increase sensitivity to doxorubicin.

The present composition may further include one or more pharmaceutically acceptable carriers, which includes but does not limited to, saline, sterilized water, Ringer's solution, buffered saline, dextrose solution, maltodextrin solution, glycerol, ethanol, liposome. If desired, the composition may further include antioxidant, buffer, antibacterial agents, and other additives known in the art to prepare pharmaceutical compositions. The present composition may be formulated into injectable formulations or oral formulations such as capsules, granules, or tablets by methods known in the art using one or more of diluents, dispersing agents, surfactants, binders and lubricants. Also encompassed for the present invention is a target specific composition combined with an antibody or other ligands that specifically recognize a molecule present on a target tissue or organ of interest. Further latest edition of Remington's Pharmaceutical Science (Mack Publishing Company, Easton Pa.) may be referred for the preparation and formulation of pharmaceutical composition.

The present composition can be administered by various routes known in the art such as oral or parenteral delivery for example intravenous, subcutaneous, or intraperitoneal injections or delivery through patch, nasal or respiratory patches. In one embodiment, injections are preferred. Desirable or optimal dosage may vary among patients depending on various factors such as body weight, age, sex, general condition of health, diet, severity of diseases, and excretion rate. Dosages used for known HIF-2α inhibitors may be referred. Where siRNA, miRNA, antisense oligonucleotides, shRNA are used, parenteral deliveries are preferred. The typical unit dosage includes but does not limit to for example about 0.01 mg to 100 mg a day. Typical daily dosage ranges from about 1 µg to 10 g and may be administered one or multiple times a day.

As used herein, the term "therapeutically effective amount" or "effective amount" refers to the amount of a therapy, which is sufficient to treat, attenuate, reduce the severity of chondrosarcoma, reduce the duration of chondrosarcoma, prevent the advancement of chondrosarcoma, cause regression of chondrosarcoma, ameliorate one or more symptoms associated with chondrosarcoma, or enhance or improve the therapeutic effect(s) of another therapy. The exact amount of HIF-2α inhibitor or cell therapeutic agents may vary depending the desired effects.

The optimal amount can be readily determined by one of skill in the art, including the type of disease, the severity of the disease, the content of other ingredients in the composition, the type of formulation, and the patient's age, weight, general health status, sex and diet, It can be adjusted according to various factors including the time of administration, route of administration and secretion rate of the composition, duration of treatment, and drugs used simultaneously.

The present disclosure is based in part on the discovery that HIF-2α plays an important role in the initiation and development of malignant chondrosarcoma, and thus by screening the agents that targets HIF-2α, therapeutic agents for chondrosarcoma, particularly malignant chondrosarcoma, particularly dedifferentiated chondrosarcoma may be developed.

In the present disclosure, it was found that HIF-2α regulates the transcription of MMP1, MMP2 and MMP9. An important event leading to chondrosarcoma metastasis is the destruction of the surrounding layer of bone-specific extracellular matrix (ECM) by catalytic enzymes such as matrix metalloproteinases (MMPs). Indeed, in the present disclosure, it was found that HIF-2α induced substantial upregulation of MMP1, MMP2 and MMP9 (FIG. 4C), and overexpression of HIF-2α increased the total MMP activity of chondrogenic sarcoma cells by approximately 3 times, and the knock-down of HIF-2α substantially reduced the degradation of the underlying matrix. These results indicate that HIF-2α directly up-regulates a subset of the MMP family proteins that promote the breakdown of the surrounding bone matrix and enable the initial escape of chondrosarcoma cells from the primary tumor.

Thus, for screening the agents that target HIF-2α or for testing the efficacy of HIF-2α inhibitors, the expression level of MMP1, MMP2 and/or MMP9 may be measured. And when the expression level thereof was reduced, the agents tested is determined to be effective for treating chondrosarcoma. MMP1, MMP2 and MMP9 are known proteins and can be found in NCBI: MMP1: NP_001139410.1, NP_002412.1; MMP2: NP_001121363.1, NP_001289437.1, NP_001289438.1, NP_001289439.1; and MMP9: NP_004985.2

In the present disclosure, by analyzing CNA of EPAS1 (Endothelial PAS domain containing protein 1, UniProtKB-Q99814) loci analyzed by GLAD, it was found that the patients with increased number of CNA of EPAS1 have poor prognosis compared to the patients without the increase. Patients with the increase of CNA of EPAS1 have poor prognosis in both overall and non-recurring survival rates. This can be advantageously used for screening high risk patients having chondrosarcoma with poor prognosis by analyzing the genome changes of the genes in HIF-2α pathway.

Thus in other aspect, the present disclosure relates to a method of determining the prognosis of a patient with chondrosarcoma by analyzing/determining or detecting the CNA (Copy Number Alteration) of EPAS1 loci from the biological sample obtained from the patients. When the CNA from the patients is increased compared to that from normal control, the patients are determined to have a poor prognosis. The method of analyzing/detecting CNA is known in the art and can be performed without difficulty in view of what is described herein and known in the art.

In the present disclosure, it was found that the concentration of HIF-2α has increased or overexpressed in chondrosarcoma, particularly dedifferentiated chondrosarcoma.

Thus, in other aspect, the present disclosure is related to a method of diagnosing chondrosarcoma in a sample from the subject in need thereof. When the concentration of HIF-2α or its activity is increased compared to that of the normal control, it is determined that the subject is affected with chondrosarcoma.

In one embodiment, the detection of HIF-2α may be performed at the level of mRNA or protein, the methods for which are known in the art and include, but are not limited thereto, for example nucleic acid amplification such as PCR and norther blot for mRNA detection, and immune assays such as western blot using antibodies specific to HIF-2α for protein detection.

In one embodiment, the detection of HIF-2α may be a detection of the detection of HIF-2α activity, which may be accomplished by transcriptional regulation of downstream gene. Such method of measuring the transcriptional activity of HIF-2α may be done by detecting the expression level of MMP1, MMP2 and/or MMP9 as described above.

The biological sample which may be used in the present methods includes tissue from primary cancer, or metastasis tissue of a primary cancer or surrounding tissue thereof. Or blood sample, any other tissue from patients from which nucleic acids are extracted.

The present disclosure is further explained in more detail with reference to the following examples. These examples, however, should not be interpreted as limiting the scope of the present invention in any manner.

EXAMPLES

Human samples. Human specimens were obtained from the National Cancer Institute Cooperative Human Tissue Network (CHTN). Written informed consents were obtained from all participants. Bone and cartilage tumor tissue arrays of various clinical stages and relevant normal bone and cartilage tissue arrays (T261a and OS805) were obtained from the US Biomax, Inc. All histological and immunohistochemical specimens were evaluated independently by two pathologists with specific expertise in human sarcomas. The pathologists were blinded to the labeling of the specimens.

Mice and experimental systems. Female athymic nude mice (BALB/c nu/nu, 5 weeks old) were purchased from Daehan-Biolink Co. and housed in individually ventilated cages. Mice were maintained under pathogen-free conditions. Food and water were provided after their sterilization. For in vivo experiments, at least five mice per experimental condition were used. Animals were randomly allocated to each experimental group, and the treatment allocation was blinded. In the orthotopic injection model, SW1353 cells were trypsinized and resuspended in PBS after centrifugation. The number of cells was adjusted to $1 \times 10^6$ cells per 25 μl. For SW1353 cells that stably overexpressed eGFP or HIF-2α, cell number was adjusted to $1 \times 10^5$ cells per 25 μl. Cells were mixed with 25 μl of Geltrex (Thermo Fisher Scientific, Geltrex™ LDEV-Free Reduced Growth Factor Basement Membrane Matrix). Before the procedure, mice were anesthetized. Skin was incised using a scalpel, and a single 0.35-mm diameter hole was drilled through the cartilage of the upper right tibia with the aid of sterile H-files (MANI, 28 mm #70). Subsequently, 10 μl of cell mixture was slowly injected with a 30-gauge microsyringe needle through the hole. The hole was sealed using surgical wax, and the surgery site was extensively rinsed with sterile PBS to wash out any spilled cell mixture. As the last step of the surgical procedure, the cutaneous wound was sutured. After the chosen experimental periods, mice were sacrificed, and total hindlimbs were dissected. For lung specimens, PBS was instilled through the trachea, and all specimens were processed for histomorphometric and immunohistochemical analysis. For the adjuvant chemotherapy studies, two weeks after the orthotopic injection of chondrosarcoma cells, mice were injected intraperitoneally with or without 2 mg/kg cisplatin in the presence or absence of 20 mg/kg TC-S7009 (Tocris) dissolved in Kolliphor EL (castor oil, 10% v/v, Sigma Aldrich, C5135). Vehicle solution was composed of DMSO, PBS, and Kolliphor EL (10% v/v). Chemotherapy cocktails were administered to mice twice weekly for four weeks.

Cell culture. Chondrosarcoma cell lines SW1353 and OUMS-27 were purchased from ATCC and JCRB Cell Bank, respectively, maintained in 3% $O_2$ at 37° C., and cultured in DMEM (WelGENE Inc., LM001-05) supplemented with 10% FBS (Gibco, 26140079) and 1% antibiotics. For the selection of stable cell lines, $1 \times 10^3$ cells were seeded in 100 mm dishes and incubated for approximately two weeks until colonies became visible, and they were supplied with fresh media every three days. Visible colonies were individually isolated using cloning rings. Single colony-forming cells were trypsinized, seeded into 24-well plates, and gradually expanded to 100 mm dishes. Transfection was performed with METAFECTENE PRO (Biontex, T040) according to the manufacturer's protocol. Small interfering RNAs (siRNAs, Bioneer) used for RNA interference experiments are listed in Table S9. All siRNAs were purchased from Bioneer. All cell lines were tested and authenticated using short-tandem repeat (STR) profiling by the Korean Cell Line Bank and were free of *mycoplasma* contamination. None of the cell line stocks used in this study was found in the database of commonly misidentified cell lines listed by ICLAC.

Histology, immunofluorescence, and immunohistochemistry. Bone tissue samples of the mice were fixed in 4% paraformaldehyde in PBS, decalcified in 8% nitric acid for 8 hours, and then neutralized in 5% sodium sulfate solution overnight. Lung tissues were fixed in 4% paraformaldehyde solution. All samples were dehydrated with graded ethanol, embedded in paraffin, sectioned at 5-μm thickness, and dried overnight. For histological or immunohistochemical staining, sections were deparaffinized in xylene and rehydrated. Sectioned samples were stained with H&E or Safranin-O. For immunostaining, antigens were retrieved upon incubation in citrate buffer (pH 6.0) at 60° C. for 1 h. Samples were blocked with 1% BSA in PBS and incubated with primary antibodies overnight at 4° C. For immunofluorescence, samples were incubated with the secondary antibody for 1 h at room temperature, followed by a 10 min incubation with 1 μg/ml DAPI. For immunohistochemistry, samples were incubated with 0.3% $H_2O_2$ for 5 min at room temperature. Tissues samples were then incubated with the biotinylated secondary antibodies for 1 h at room temperature, followed by a 30 min incubation with streptavidin-HRP. Signal was developed using an alcohol soluble chromogen, aminoethyl carbazole (AEC; DAKO). Tissues were stained with Mayer's hematoxylin (DAKO) for 30 sec and placed in 0.08% $NH_4OH$ for 30 sec. Histological or immunochemical staining images were acquired with the DS-Ri2 camera (Nikon) connected to a Nikon Eclipse Ni-U upright microscope and analyzed. For immunofluorescence detection, the immunostained tissues were imaged with a laser scanning confocal microscope (Carl Zeiss, LSM700).

Microarray. SW1353 cells ($3 \times 10^5$) were transfected with control, HIF1A, or EPAS1 siRNAs. Three biological replicates were used for each group. cDNA was synthesized using the GeneChip WT (Whole Transcript) Amplification kit as described by the manufacturer. Microarray services were provided by Macrogen Inc. and performed using GeneChip® Human Gene 2.0 ST Array (Affymetrix). Array data export processing and analysis were performed using the Affymetrix® GeneChip Command Console® Software (AGCC). To determine differentially expressed genes between comparison samples, |log$_2$(fold change)|>0.263 and P-value (paired t test)<0.05 were used as cutoffs.

Antibodies and reagents. The HIF-2α inhibitor TC-S7009 (5243) was obtained from Tocris. Kolliphor EL (C5135), cisplatin (C2210000), and Nutlin-3a (SML0580) were purchased from Sigma Aldrich. ABT-888 (11505) was purchased from Cayman. Anti-HIF-2α antibody (sc-13596), normal mouse IgG (sc-2025), and goat anti-mouse IgG-B (sc-2039) were purchased from Santa Cruz Biotechnology. Anti-human mitochondria antibody (MAB1273) was purchased from Millipore. Anti-HIF-2α antibody (NB100-122) was purchased form Novus Biologicals. Biotin-SP-conjugated goat anti-rabbit IgG was purchased from Jackson ImmunoResearch Labs. Anti-rabbit IgG Alexa Fluor 647 (A-31573), anti-mouse IgG Alexa Fluor 594 (A-21203), and anti-goat IgG Alexa Fluor 488 (A-11055) were purchased from Thermo Fisher Scientific.

Weighted gene co-expression network analysis (WGCNA). The weighted network construction was performed using the WGCNA R package from Bioconductor, as described in Langfelder and Horvath (Langfelder P, Horvath S. Eigengene networks for studying the relationships between co-expression modules. Bmc Syst Biol 1, 54 (2007). The WGCNA builds directed co-expression networks of genes across microarray samples; the expression profiling analyzed in this study was from 17 fresh frozen chondrosarcoma biopsies (GSE12475). Nodes of the network corresponded to genes, and a pair of nodes were connected through an edge if there was a co-expression relationship between them (Langfelder P, Zhang B, Horvath S. Defining clusters from a hierarchical cluster tree: the Dynamic Tree Cut package for R. Bioinformatics 24, 719-720 (2008)).

Ingenuity pathway analysis (IPA) of patient transcriptome data. IPA (Qiagen, https://www.qiagenbioinformatics.com/products/ingenuity-pathway-analysis/) was used to conduct the diseases and functions analysis and to identify upstream regulators. The algorithms developed for use in IPA have been described in Kramer et al (Kramer A, Green J, Pollard J, Jr., Tugendreich S. Causal analysis approaches in Ingenuity Pathway Analysis. Bioinformatics. 2014; 30(4):523-530). To analyze the enrichment P-value and activation z-score of cancer-relevant genesets, the diseases and functions analysis of IPA was performed on M1 (263 genes), M2 (265 genes), and M3 (418 genes) module datasets. The regulator-effector analysis was performed to identify upstream regulators of the M1 module. For calculation of the activation z-score, module membership values from WGCNA results were used as inputs.

Gene set enrichment analysis (GSEA). GSEA was performed with default parameters as described in Aravind et al (Gene set enrichment analysis: a knowledge-based approach for interpreting genome-wide expression profiles. Proc Natl Acad Sci USA 102, 15545-15550 (2005)). Nominal P-value<0.05 was considered significant. Hallmark genesets were obtained from the MSigDB database (http://software.broadinstitute.org/gsea/msigdb). Invasion of tumor and cancer stem cell genesets were obtained from the IPA.

PCA analysis. Based on the HIF-2α target genes expression profiles, the PCA was performed using the R package to predict the HIF-2α activation state in the chondrosarcoma patients (FIG. 7 B).

Drug Interaction Studies. For analysis of combination index (CI), SW1353 cells were pretreated with vehicle, 10 μM Nutlin-3a, 10 μM ABT-888, or 10 μM TC-S7009 for 48 h and additionally treated with 0.2, 0.5, 1, 2, or 5 μg/ml cisplatin or left untreated for 72 h. Cell viability was measured by the MTT assay. CI was calculated using the Compusyn software version 1.0, and synergistic effects were determined by the Chou-Talalay method (Chou T C. Drug Combination Studies and Their Synergy Quantification Using the Chou-Talalay Method. Cancer Res. 2010; 70(2):440-446). Drug combination at a non-constant ratio was used to calculate CI. For apoptosis analysis, SW1353 cells were pretreated with vehicle, 10 μM Nutlin-3a, 10 μM ABT-888, or 10 μM TC-S7009 for 48 h and additionally treated with 5 μg/ml cisplatin for 24 h. Subsequently, cells were stained with the Annexin V-FITC Apoptosis Detection Kit (Sigma Aldrich, APOAF) according to manufacturer's protocol. Flow cytometry analysis was performed on a FACSCanto II flow cytometer (BD Biosciences).

Copy number alteration (CNA) analysis. Genomic profiles were analyzed using the Gain and loss analysis of DNA software (GLAD package from Bioconductor) as described in Hupe et al (Hupe P, Stransky N, Thiery J P, Radvanyi F, Barillot E. Analysis of array CGH data: from signal ratio to gain and loss of DNA regions. Bioinformatics 20, 3413-3422 (2004)). A label (Gain, Stable, or Loss) was assigned to each region, based on its median DNA copy number. Gain or loss was defined as a positive or negative smoothing value, respectively.

Lentivirus production and transduction. For the construction of the vector overexpressing HIF-2α, the human HIF-2α coding region of the pcDNA3-EPAS1 plasmid (Addgene, plasmid #18950) was subcloned into the pLJM1-eGFP vector (Addgene, plasmid #19319). For the construction of vectors to use in the RNA interference assays, the sequences of scramble and EPAS1 shRNA (Shen C, et al. Genetic and Functional Studies Implicate HIF1 alpha as a 14q Kidney Cancer Suppressor Gene. Cancer Discovery 1, 222-235 (2011)) were inserted into the pLKO.1 puro plasmid (Addgene, plasmid #8453). The primer sequences used for cloning are listed in Table S9. To produce lentiviruses, HEK293T cells were seeded at $6.5 \times 10^6$ cells per 100 mm culture dish and incubated for 24 h. The vectors for HIF-2α overexpression or knockdown were co-transfected with the psPAX2 (Addgene, plasmid #12260) and pMD2.G (Addgene, plasmid #12259) vectors. After three days, supernatants were harvested and filtered using 0.45-μm filters. For lentiviral transduction, cells were infected with lentiviruses for 24 h in the presence of 8 μg/ml polybrene (Sigma Aldrich, H9268). Infected cells were selected using 1 μg/ml puromycin for three days.

Transwell invasion assay. The invasion assay was performed using Transwell (BD Falcon, pore size, 8 μm, PET) in 24-well plates. Filters were coated with 20 μg of Geltrex (Thermo Fisher Scientific) in 20 μl of serum-free DMEM and dried for 4 h in a sterile environment. Prior to the invasion assay, SW1353 and OUMS-27 cells were starved for 12 h in serum-free DMEM. Immediately before seeding the cells, the dried transwells were rehydrated with 25 μl of serum-free DMEM for 1 h at 37° C. Starved cells were trypsinized, centrifuged, and resuspended in serum-free DMEM. Approximately $1 \times 10^5$ cells in 200 μl of serum-free DMEM were placed in each transwell and 2 ml of DMEM supplemented with 10% FBS was placed in each 24-well plate. The plates were incubated for 48 h at 37° C., fixed in 4% paraformaldehyde for 2 min, permeabilized in 100% methanol for 20 min, and stained with 0.1% crystal violet in 10% ethanol for 20 min. Cells on the upper side of the transwell were removed with cotton-tipped swabs. During each of the staining steps, the transwells were washed with PBS. The underside of the transwells was examined under a microscope, and images were taken using the DS-Ri2 camera. Image fields were randomly chosen, and invading cells were counted using the ImageJ software (National Institutes of Health).

Sphere formation assay. SW1353 and OUMS-27 cells were suspended in DMEM-F12 medium supplemented with 2% of B27 supplement (Thermo Fisher Scientific), 20 ng/ml EGF (Invitrogen), and 20 ng/ml basic fibroblast growth factor (bFGF; Peprotech). For experiments using SW1353 cells overexpressing eGFP or HIF-2α, cells were suspended in DMEM-F12 medium in the absence of the above supplements. Cells were then seeded in 24-well Ultra-low attachment plates (Corning) at a density of $1 \times 10^4$ cells per well. Four days later, fresh medium was added in each well. Seven days later, spheres were analyzed by the sphere diameter and the number of spheres larger than 50 μm (Axio Observer Z1, Zeiss). In relation to the diameter of the spheres, three representative fields per well were imaged, and diameters were measured using the AxioVision software (Zeiss): the three longest diameters per image field for each group were recorded. The distribution of the sphere diameters was plotted using the notched Box-and-Whisker plot originally invented by Tukey. The sphere formation assay was repeated at least six times.

Gelatin degradation assay. SW1353 cells were seeded on coverslips coated with Oregon Green 488-conjugated gelatin (Life Technologies) at $4 \times 10^4$ cells per well. Briefly, coverslips were treated with 50 μg/ml poly-D-Lysine (Corning) for 20 min followed by 0.5% glutaraldehyde (Junsei Chemical) for 15 min on ice. Treated coverslips were coated at 37° C. with pre-warmed 200 μg/ml Oregon Green 488- conjugated gelatin for 10 min in the dark, treated with 5 mg/ml NaBH$_4$ for 15 min, and extensively washed with 70% ethanol and PBS. Cells were incubated for 18 h after seeding. For imaging gelatin degradation, cells were fixed with 50% methanol (v/v) and 10% acetic acid (v/v) solution for 10 min and stained with DAPI. For each coverslip, three fields were imaged at 20× magnification using a fluorescence microscope (EVOS FL Cell Imaging System, Thermo Fisher Scientific). To quantify gelatin degradation, the area of degradation in each field was measured by color-thresholding, using the ImageJ software.

Luciferase assay. HIF-2α activity was determined by reporter gene assay. SW1353 cells were transfected with 1 μg of a reporter vector containing hypoxia responsive element repeats. The thymidine kinase promoter-*Renilla* luciferase reporter plasmid (pRL-TK) was used as a control for measuring transfection efficiency. For HIF-2α overexpression, the pcDNA3-EPAS1 (Addgene, plasmid #18950) plasmid was transfected using METAFECTENE PRO (Biontex, T040). Twenty-four hours after transfection, cells were treated with TC-S7009 for an additional 24 h. Luciferase activity was measured using luciferin and normalized by *Renilla* luciferase activity.

Migration assay. SW1353 and OUMS-27 cells were cultured in a 6-well plate at a density of 5×10$^5$ cells per well. When cells achieved 90% confluence, a wound was made with a sterile yellow tip. Cells were washed with PBS three times and incubated in fresh media with 1% FBS for 36 h. Every 12 h, randomly selected fields were captured by a digital camera under a microscope.

Colony formation assay. SW1353 cells were suspended in DMEM supplied with 10% FBS and seeded in 6-well plates; 1×10$^3$ and 500 cells were seeded in each well for the knockdown and overexpression experiments, respectively. The medium was changed every three days for 14 days. OUMS-27 cells were suspended in DMEM supplied with 10% FBS and seeded in 6-well plates; 5×10$^3$ and 1×10$^3$ cells were seeded for the knockdown and overexpression experiments, respectively. The medium was changed every three days for 21 days. Colonies were fixed in 4% paraformaldehyde solution for 2 min and permeabilized in 100% methanol for 20 min. Following, colonies were stained in a 0.1% (w/v) crystal violet solution for 20 min.

MMP activity assay. Measurement of MMP enzyme activity was performed as previously described (Kim J H, et al. Matrix cross-linking-mediated mechanotransduction promotes posttraumatic osteoarthritis. Proc Natl Acad Sci USA 112, 9424-9429 (2015)). using the MMP Activity Assay Kit (Abcam) according to the manufacturer's protocol. Briefly, 1 ml of conditioned medium containing MMPs secreted from SW1353 cells was collected and concentrated to 100 μl. The substrate solution (50 μl), containing the fluorescence resonance energy transfer (FRET) peptide whose cleavage by MMPs generates green fluorescence, was mixed with a 50 μl aliquot of the sample. Fluorescence intensity was detected kinetically every 5 min for 1 h with excitation at 488 nm and emission at 530 nm, using a Spectramax Gemini microplate fluorescence reader (Molecular Device).

Quantitative RT-PCR (qRT-PCR). Total RNAs were extracted using the TRI Reagent® (Molecular Research Center, Inc.). RNAs were reverse-transcribed using EasyScript Reverse Transcriptase (Transgen Biotech); qRT-PCR was performed using the SYBR Green PCR Master Mix (Enzynomics) and processed using a StepOnePlus Real-Time PCR System (Applied Biosystems). PCR condition began with an initial denaturation step of 10 min at 95° C., followed by 40 cycles of PCR consisting of 20 sec at 95° C., 1 min at 60° C. Melt curves were collected at the final step of the final stage by increasing temperature from 60° C. to 95° C. The PCR data were analyzed using the $2^{-\Delta\Delta CT}$ method, and HPRT was used as the housekeeping gene. The primer sequences are listed in Table 2.

Statistics. Statistical significance of differences between two groups was assessed by a two-tailed unpaired Student's t test. For multiple group comparisons and repeated measures, analysis of variance (ANOVA), followed by the post-hoc least significant difference (LSD) test, were used. Data are expressed as mean±SEM. $P<0.05$ was considered significant. Survival curves were estimated based on the Kaplan-Meier method and compared using the log-rank test. For the measurement of correlation between mRNA expressions, R and P-values were calculated by Pearson correlation coefficients. Statistical analysis was performed using the SPSS version 22 statistical software (IBM). For the comparison of sphere diameters, Tukey distribution bars were used to emphasize data range distribution, and the notches of each box were analyzed. Center lines indicate the median, and box limits indicate the $25^{th}$ and $75^{th}$ percentiles as determined by the R software. Whiskers extend 1.5 times the interquartile range from the $25^{th}$ and $75^{th}$ percentiles, outliers are represented by dots, and extreme values are represented by asterisks. Notch shows 95% confidence interval of the median. Box plots were plotted using the XLSTAT software (Addinsoft).

Study approval. Before obtaining specimens, the study was approved by the Institutional Review Board (IRB) of Seoul National University (IRB No. E1611/003-008 and E1803/003-007). All animal studies were approved by the Seoul National University Institutional Animal Care and Use committees (IACUC; IACUC No. SNU-151216-2-2). We conformed to the ARRIVE guidelines (https://www.nc3rs.org.uk/arrive-guidelines) for reporting animal experiments.)

Data availability. The expression profiling and genome variation profiling data referenced during the study are available in a public repository from the NCBI (www.ncbi.nlm.nih.gov) websites. For the transcriptome analysis, the following datasets were used: chondrosarcoma patients dataset (Gene Expression Omnibus: GSE12475) (Hallor K H, et al. (2009) Genomic profiling of chondrosarcoma: chromosomal patterns in central and peripheral tumors. *Clin Cancer Res* 15(8):2685-2694), murine chondrocyte dataset (GSE73659) (Huh Y H, Lee G, Song W H, Koh J T, & Ryu J H (2015) Crosstalk between FLS and chondrocytes is regulated by HIF-2 alpha-mediated cytokines in arthritis. *Exp Mol Med* 47), and primary chondrosarcoma cells dataset (GSE47823) (Desiderio V, et al. (2013) Molecular Profiling of Human Primary Chondrosarcoma-Derived Spheres Reveals Specific and Target Genes Involved in Multidrug Resistance and Metastasis. *J Carcinogene Mutagene* 5(1)). For copy number alteration analysis, the following dataset was used: chondrosarcoma patients dataset (GSE12532) (Hallor K H, et al. ibid) Original transcriptome data sets will be deposited in the Gene Expression Omnibus (GEO).

Example 1: Identification that HIF-2α is a Predicted Transcriptional Regulator of Cancer Malignancy in Patients with Chondrosarcoma To extract a characteristic gene expression pattern underlying chondrosarcoma malignancy, we conducted weighted gene co-expression network analysis (WGCNA) based on the transcriptome dataset of patients with chondrosarcoma.

Figure 1A:
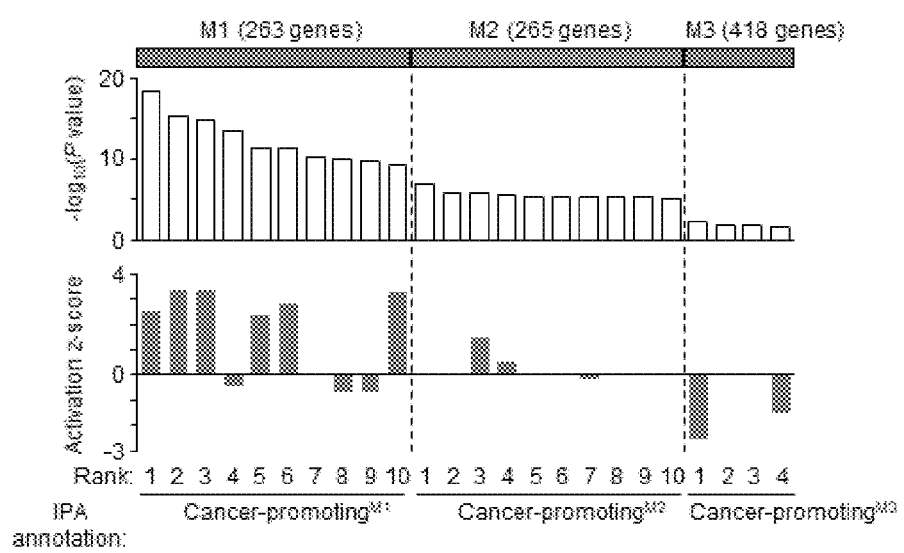
FIG. 1A to FIG. 1H indicate that HIF-2α is an upstream regulator of a gene module governing chondrosarcoma.
Figure 1B:
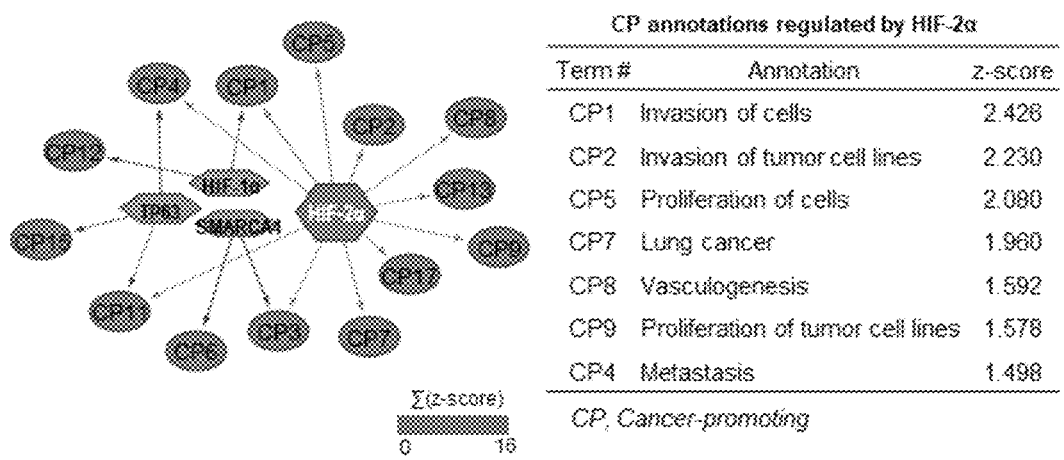
Figure 1C:
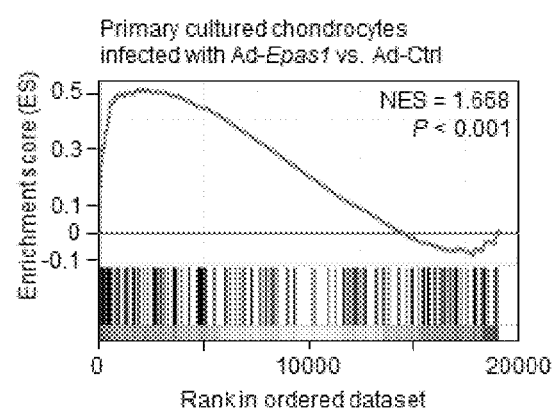
Figure 1D:
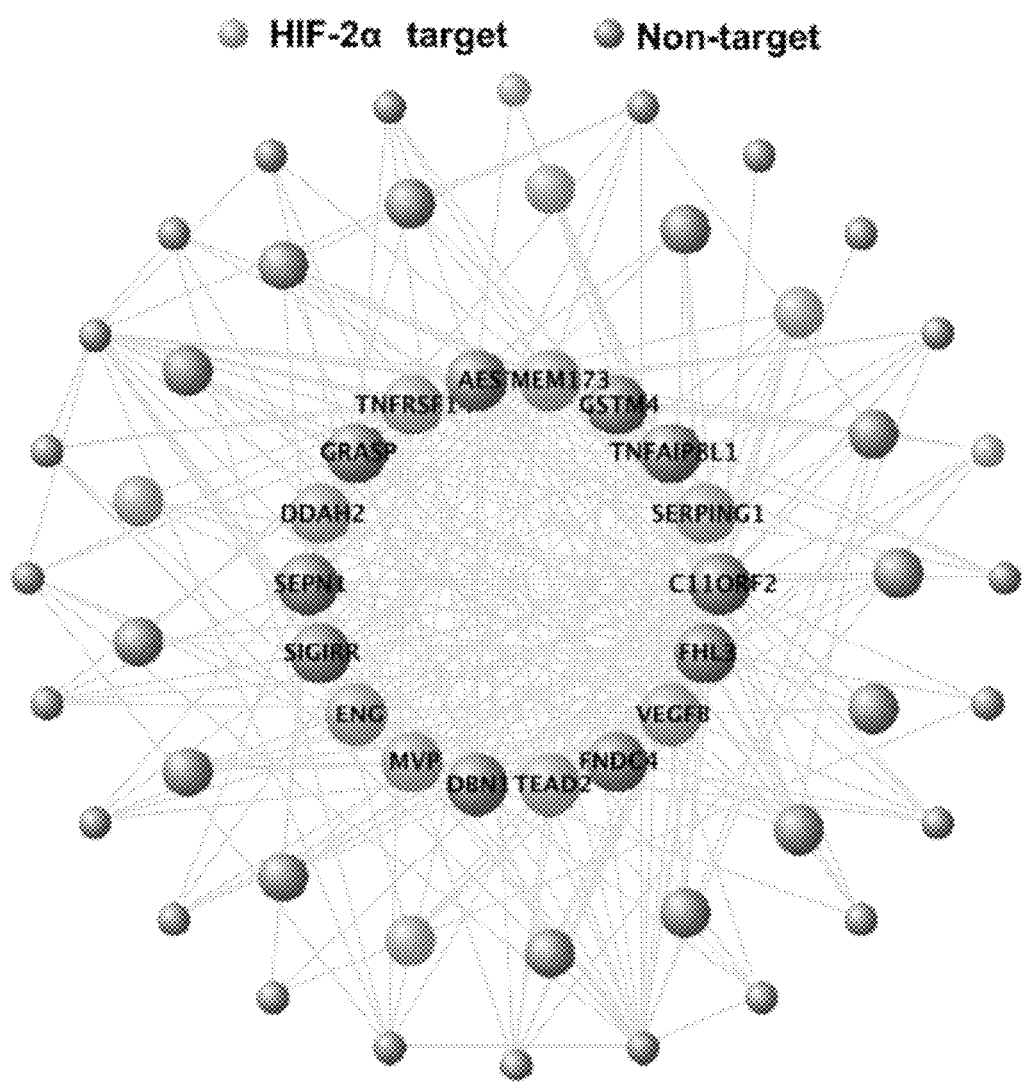

Three distinct gene modules, each consisting of highly correlated module membership genes, were identified (FIG. 1A). We analyzed each module by calculating enrichment P-values and the activation z-scores for all cancer-relevant genesets obtained from Ingenuity Pathway Analysis (IPA) (Kramer A, et al. Causal analysis approaches in Ingenuity Pathway Analysis. Bioinformatics. 2014; 30(4):523-530). The M1 module, comprising 263 genes, showed significant enrichment patterns for cancer-promoting annotations such as 'growth of tumor', 'metastasis', and 'advanced malignant tumor', with most of them being in the highly activated state. In contrast, the M2 and M3 modules had a relatively lower extent of overlap with cancer-promoting terms (FIG. 1A and Table S2). We therefore defined the M1 module as a functional geneset whose expression dictates malignant characteristics of chondrosarcoma. We performed IPA upstream regulator analysis to predict the transcriptional regulator governing the expression of M1 module genes; HIF-2α was predicted as the most potent transcription factor activating the M1 module (FIG. 1B). Indeed, our geneset enrichment analysis (GSEA) indicated that overexpression of HIF-2α in chondrocytes elicits overall upregulation of M1 module genes at the transcriptome level (FIG. 1C). Based on the WGCNA analysis, hub genes (i.e. those with high connectivity) within the M1 module gene network appear to have a strong tendency to be the transcriptional targets of HIF-2α, further supporting HIF-2α-driven collective activation of M1 module genes (FIG. 1D).

Figure 1E:
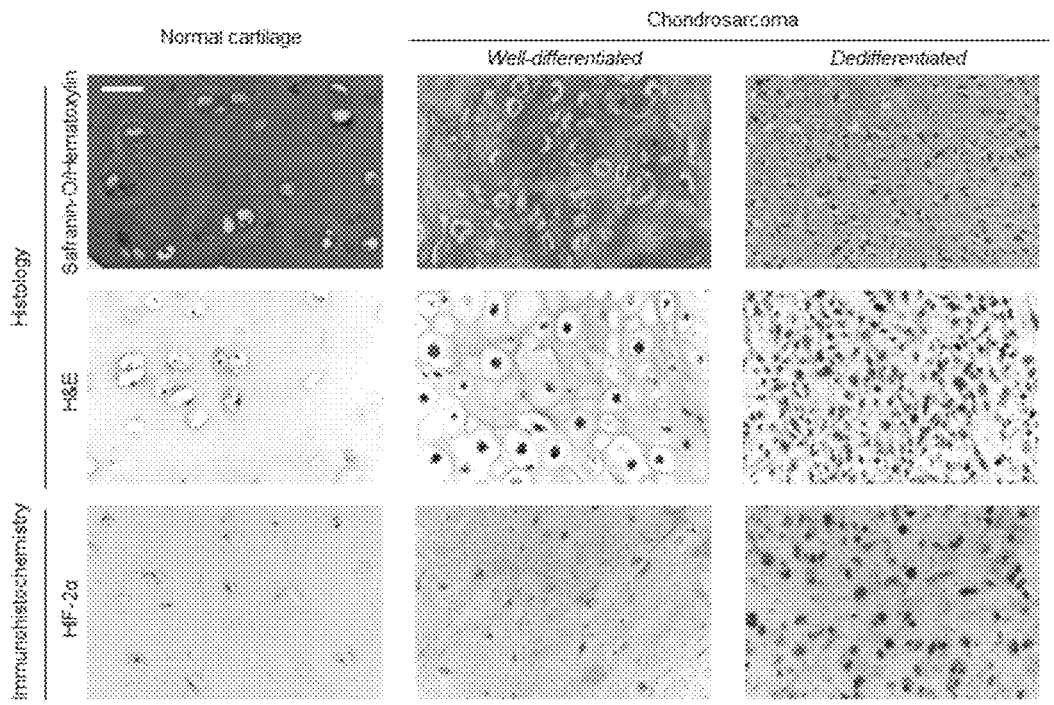
Figure 1F:
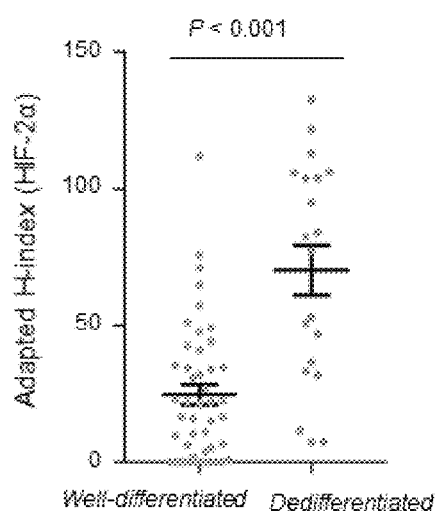
Figure 1G:
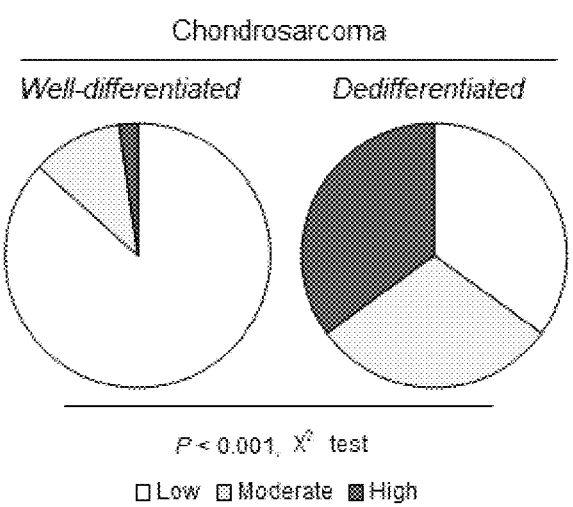
Figure 1H:
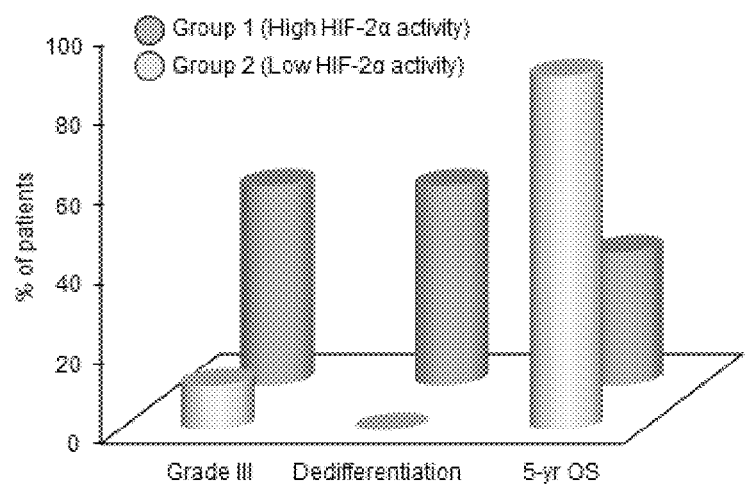

Immunohistochemistry (IHC) analysis of normal cartilage, osteochondroma, enchondroma, and chondrosarcoma tissues indicated the overall upregulation of HIF-2α protein in chondrosarcoma biopsies (FIG. 7, A). Notably, high expression of HIF-2α(was more significantly associated with dedifferentiated than well-differentiated chondrosarcoma (FIG. 1E to 1G). Therefore, we examined a possible correlation between the predicted activation states of HIF-2α and clinical outcomes in patients. We classified patients with chondrosarcoma into two groups, according to their transcription profiles of HIF-2α target genes such that group 1 is correlated with higher activation status of HIF-2α as compared to group 2 (FIG. 7, B). We then crosschecked the clinical data of the patients in each group for correlation with the HIF-2α activity. Patients in group 1 not only tended to be associated with grade III and dedifferentiated states of chondrosarcoma, but also to have poorer prognosis (FIG. 1H).

Figure 2A:
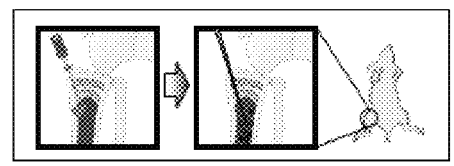
FIGS. 2A to 2F indicate HIF-2α promotes metastatic propensity of chondrosarcoma in an orthotopic mouse model.
Figure 2A:
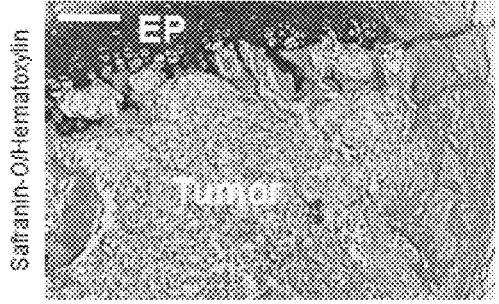
Figure 2B:
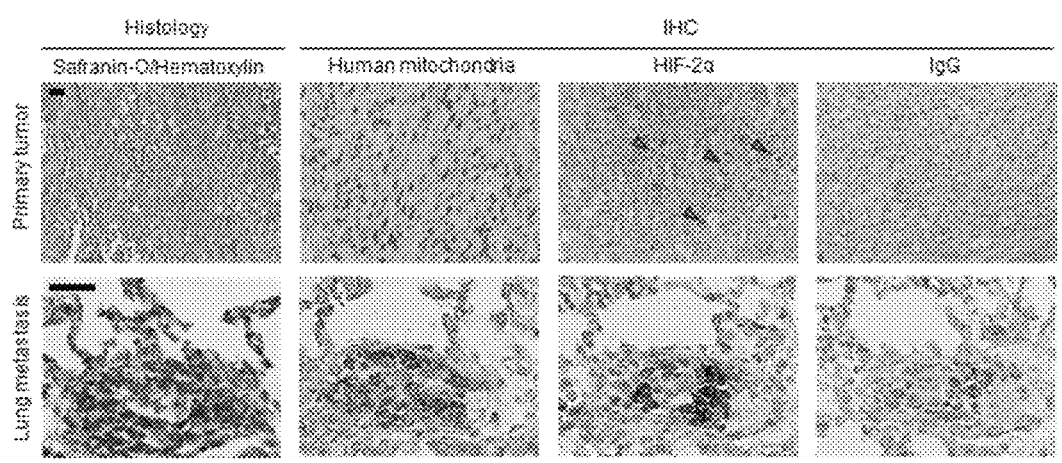
Figure 2C:
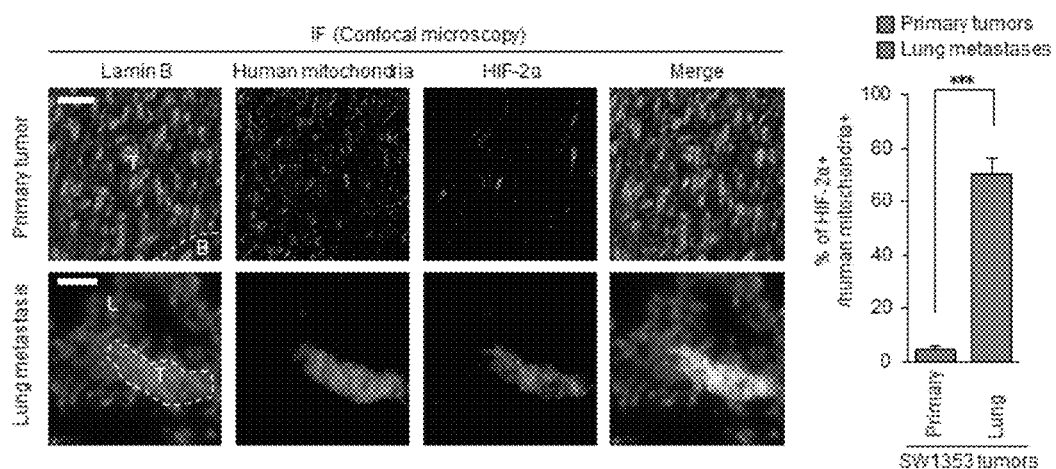
Figure 2D:
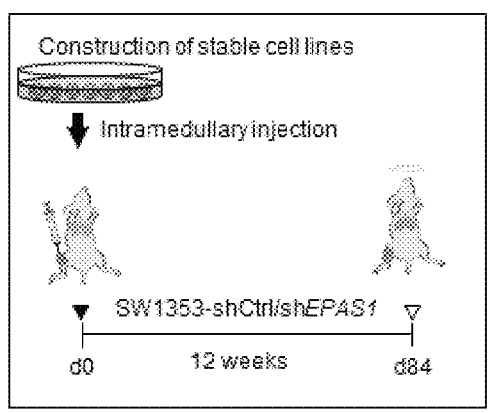
Figure 2E:
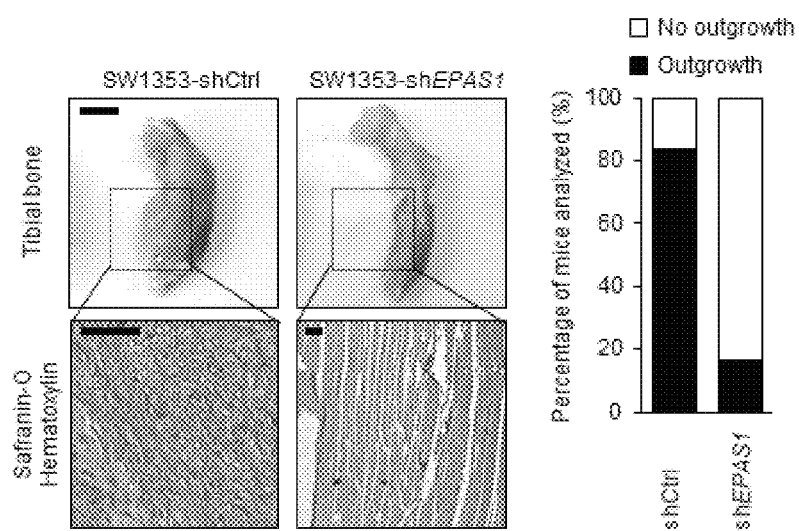
Figure 2F:
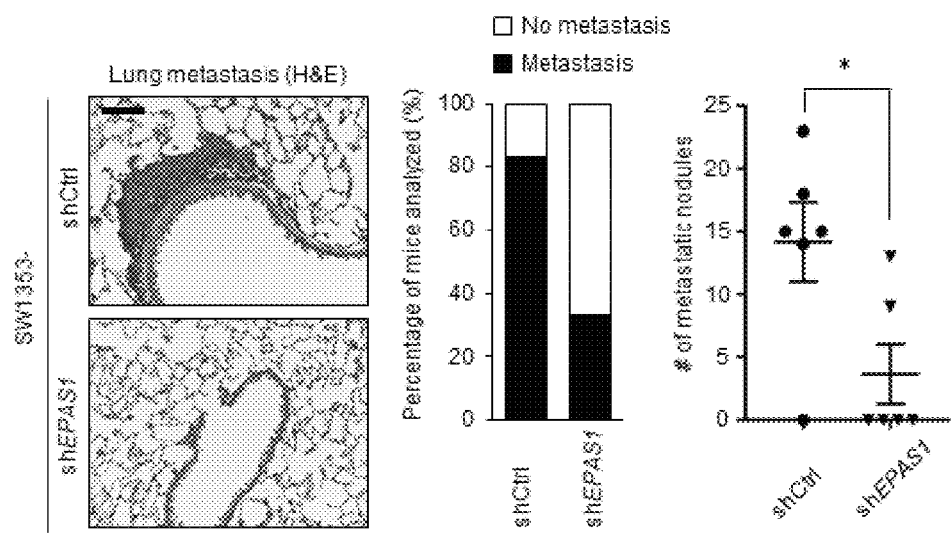

Example 2: Identification that HIF-2α Confers a Selective Advantage for Metastatic Processes in a Murine Xenograft Orthotopic Model The orthotopic mouse model of chondrosarcoma was established with the human chondrosarcoma cell line SW1353 (Clark J C M, et al. New clinically relevant, orthotopic mouse models of human chondrosarcoma with spontaneous metastasis. Cancer Cell Int. 2010; 10). Chondrosarcoma cells implanted within the tibial intramedullary canal developed into tumors by six weeks (FIG. 2A). Within these primary SW1353 tumors, considerable heterogeneity in HIF-2α expression was observed such that only a fraction of chondrosarcoma cells exhibited distinct HIF-2α positivity (FIG. 2B). We noted that the transplanted chondrosarcoma cells underwent pulmonary metastasis. Interestingly, secondary SW1353 tumors in the lung were frequently HIF-2α positive (FIG. 2B). Consistently, when HIF-2α and human mitochondria were observed with multicolor immunofluorescence (IF), the percentage of double positivity among primary and metastatic SW1353 tumors was 4.6% and 70.2%, respectively (FIG. 2C). Thus, we hypothesized that HIF-2α expression may confer chondrosarcoma cells a selective advantage for escaping their primary site and becoming metastatic. To test this possibility, we implanted SW1353 cells stably expressing shEPAS1 or control shRNA into the tibia of athymic mice (FIG. 2D). Knockdown of HIF-2α in SW1353 cells effectively reduced the occurrence of extraosseous outgrowth and pulmonary metastasis (FIGS. 2E and 2F).

Figure 3A:
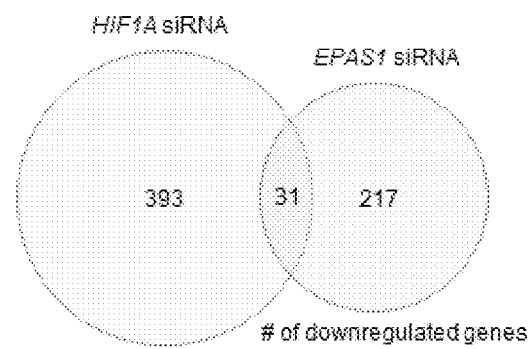
FIGS. 3A to 3D show that HIF-2α regulates cancer-relevant hallmark genesets in chondrosarcoma cells and results of the analysis of the total mRNA expression pattern in the cells in which HIF-2α expression is downregulated by siRNA. It was found that the genes that showed significant reduction in their expression by the suppression of HIF-2α expression are related to EMT (epithelial mesenchymal transition) Aoptosis, and p53 pathway, which are generally known to be related to the development and metastasis of cancer. Particularly it is known that EMT is related to metastasis of cancer and the cells with EMT are prone to metastasis, and thus this indicates that the suppression of HIF-2α can suppress the metastasis of cancer. In addition, it was found that due to the inhibition of HIF-2α, the expression of genes related to apoptosis and p53 signaling system was increased. This means that HIF-2α indirectly decreases genes involved in apoptosis and p53 signaling pathway at the cellular level. Specifically, the results indicate that inducing apoptosis through inhibition of HIF-2α or increasing the expression of genes related to the p53 signaling system can lead to reduce cancer cell proliferation and survival of cancer cells during metastasis. The p53 signaling system is generally known as a signaling system that inhibits cell growth, and p53 itself is very well known as a tumor suppressor. Therefore, the results indicate that the inhibition of HIF-2α using siRNA can inhibit the growth, metastasis, and survival of chondrosarcoma.
Figure 3B:
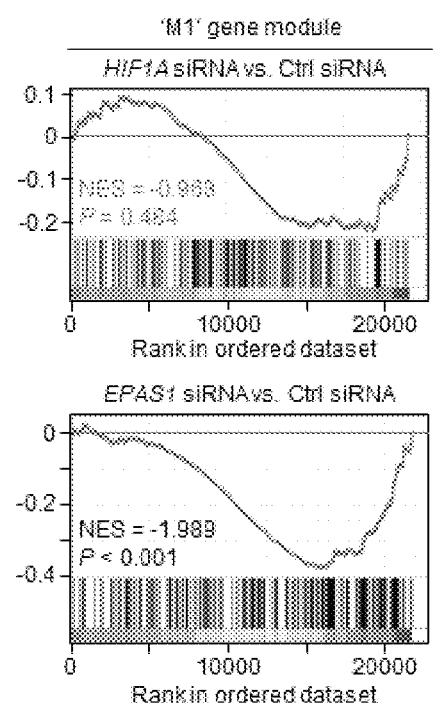
Figure 3C:
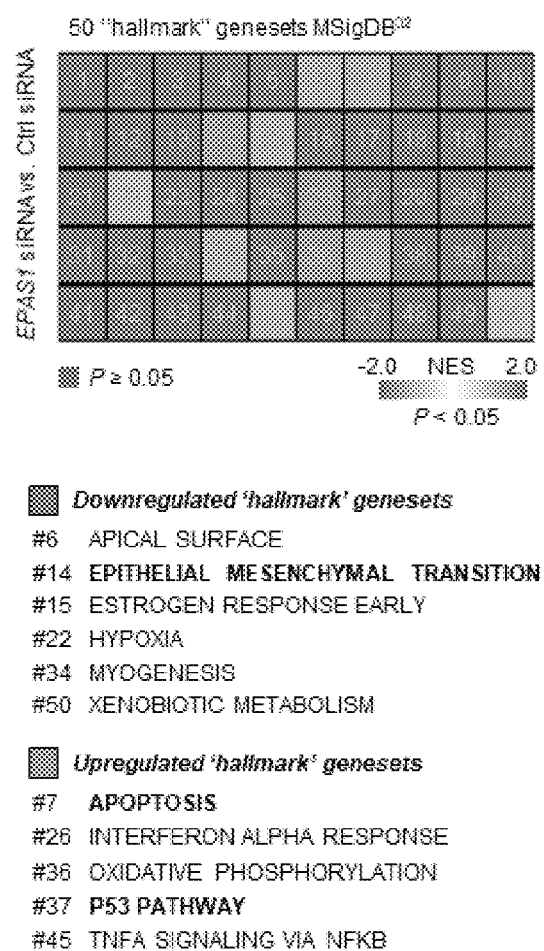
Figure 3D:
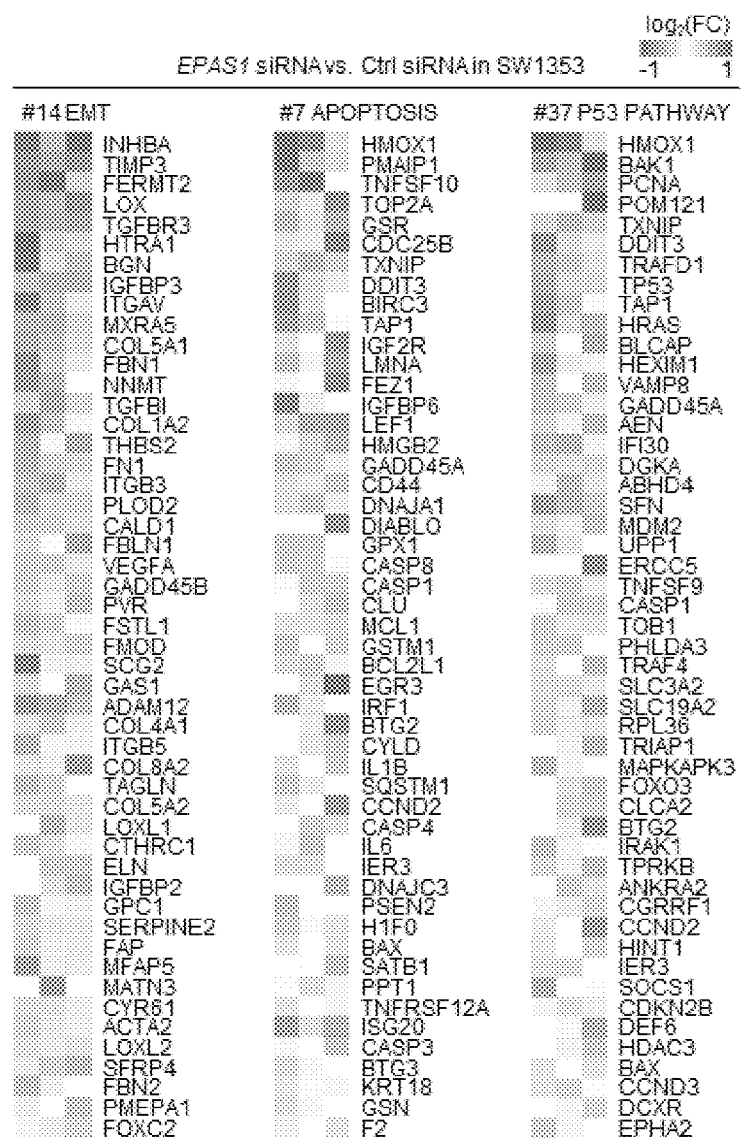

Example 3: Identification that HIF-2α-Driven Transcriptome Governs 'Hallmark' Genesets Related to Metastasis and Cell Survival To gain molecular insights into the role of HIF-2α in chondrosarcoma, we performed transcriptome analysis in SW1353 cells with or without HIF-1α or HIF-2α knockdown. In response to HIF-1α and HIF-2α knockdown, 424 and 248 genes were differentially downregulated, respectively (FIG. 3A). Interestingly, only 31 genes were commonly regulated by the two HIFs, supporting the non-redundancy of HIF-1α and HIF-2α in target gene specificity. The M1 module was downregulated overall by knockdown of HIF-2α, but not HIF-1α (FIG. 3B), further corroborating that HIF-2α is the upstream regulator of the M1 module. Pathway enrichment analysis was performed using the Molecular Signatures Database (MSigDB) 'hallmark' genesets (Liberzon A, et al. The Molecular Signatures Database (MSigDB) hallmark gene set collection. Cell Syst. 2015; 1(6):417-425.) for the HIF-2α knockdown transcriptome. Among the 50 hallmark signaling genesets, 11 annotations were significantly affected by HIF-2α knockdown (FIG. 3C). Those relevant to chondrosarcoma malignancy included 'epithelial mesenchymal transition (EMT)', 'apoptosis' and 'p53 pathway' (FIG. 3D).

Figure 4A:
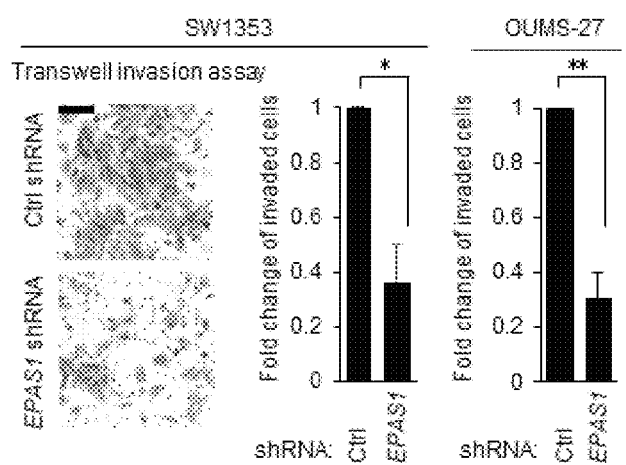
FIGS. 4A to 4I show that HIF-2α grants chondrosarcoma cells invasiveness and tumor-initiating capacity.
Figure 4B:
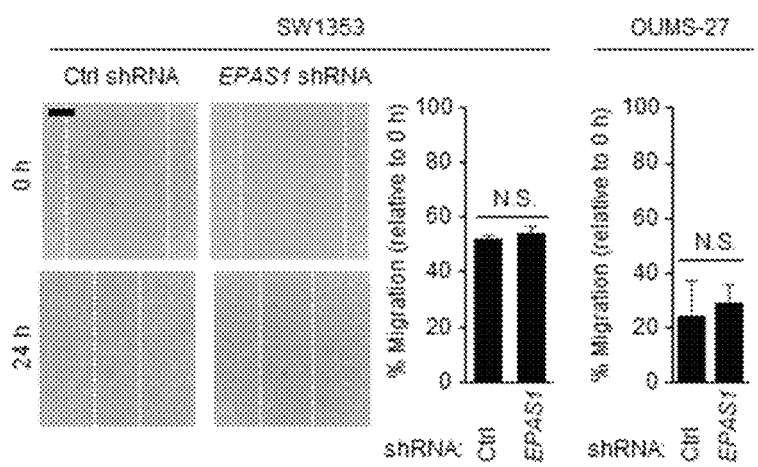
Figure 4C:
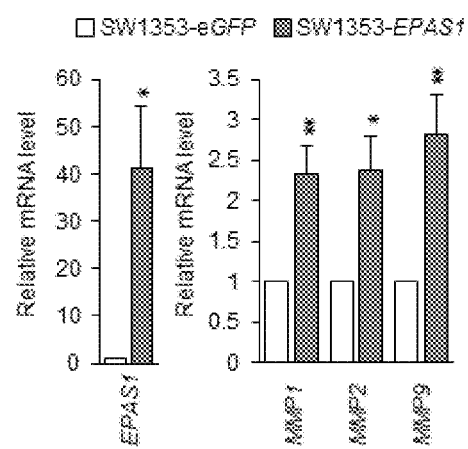
Figure 4D:
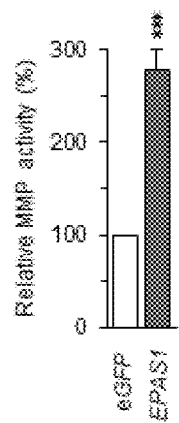
Figure 4E:
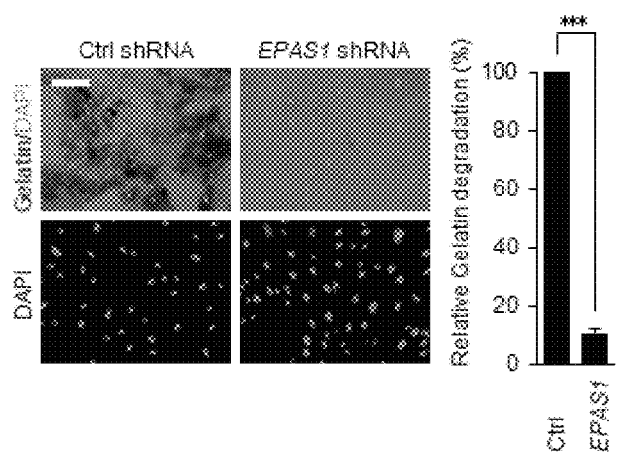
Figure 4F:
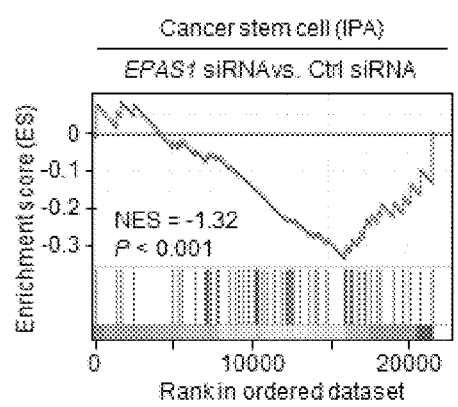

Example 4: Identification that HIF-2α Gives Rise to Metastatic Capacity by Upregulating Microenvironment-Specific ECM Degrading Enzymes Transcriptome analysis indicated that HIF-2α expression is strongly correlated with the expression of hallmark genes of EMT, a process essential for cancer cell invasion and metastasis (Egeblad M, et al. New functions for the matrix metalloproteinases in cancer progression. Nat Rev Cancer. 2002; 2(3):161-174, Friedl P, et al. Tube travel: The role of proteases in individual and collective a cancer cell invasion. Cancer Res. 2008; 68(18):7247-7249). Therefore, we tested how HIF-2α affects the invasive and migratory behaviors of the two different chondrosarcoma cell lines, SW1353 and OUMS-27. HIF-2α knockdown markedly suppressed their invasiveness (FIG. 4A), whereas their migration rate was not affected (FIG. 4B and FIG. 8A). A critical event to initiate chondrosarcoma metastasis is the destruction of the surrounding layers of bone-specific extracellular matrix (ECM) by catabolic enzymes such as matrix metalloproteinases (MMPs) (Egeblad M, et al. New functions for the matrix metalloproteinases in cancer progression. Nat Rev Cancer. 2002; 2(3):161-174, Soderstrom M, et al. Expression of matrix metalloproteinases and tissue inhibitors of metalloproteinases in human chondrosarcomas. APMIS. 2001; 109 (4):305-315). Indeed, HIF-2α caused substantial upregulation of MMP1, MMP2, and MMP9 (FIG. 4C), which specifically degrade ECM molecules abundant in the bone Indeed, HIF-2α caused substantial upregulation of MMP1, MMP2, and MMP9 (FIG. 4C), which specifically degrade ECM molecules abundant in the bone (Murphy G, et al. What are the roles of metalloproteinases in cartilage and bone damage? Ann Rheum Dis. 2005; 64:44-47). These MMPs possess HIF binding sites in their promoter regions as predicted by TRANSFAC analysis (FIG. 8B). Consistently, HIF-2α overexpression induced an approximately 3-fold increase in total MMP activity in chondrosarcoma cells whereas knockdown of HIF-2α substantially reduced the degradation of underlying substrates (FIGS. 4, D and E). HIF-2α and HIF-2α target MMPs were positively correlated in the chondrosarcoma patient transcriptomes (FIG. 8C). Conversely, these MMPs had no correlation with HIF-1α and negative correlation with HIF-3α, a posttranslational negative regulator of HIF-2α in chondrocytes (FIG. 8C). Our results suggest that HIF-2α directly upregulates a subset of MMP family proteins, which in turn facilitates the degradation of the surrounding bone matrix and allows initial escape of chondrosarcoma cells from the primary tumor.

Figure 4G:
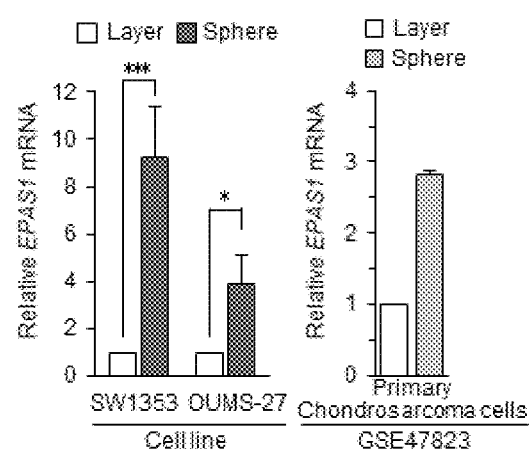
Figure 4H:
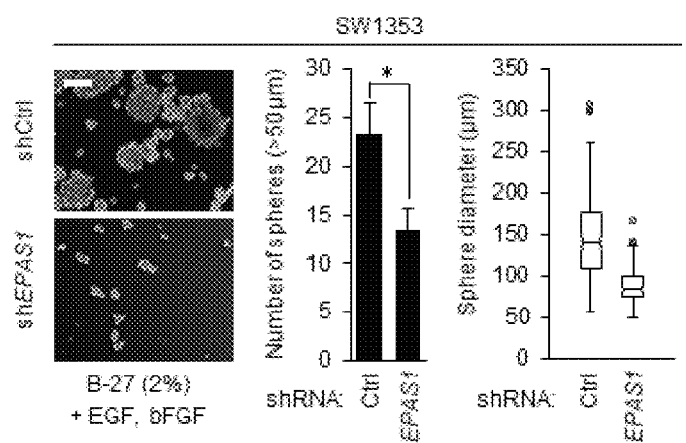
Figure 4I:
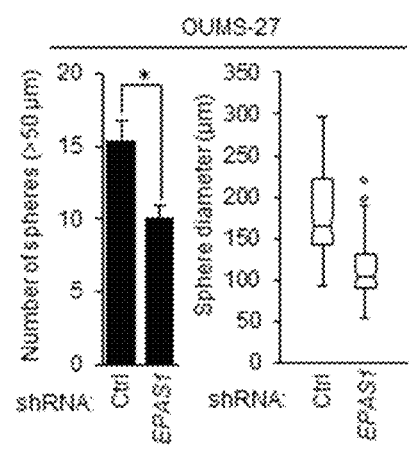
Figure 4J:
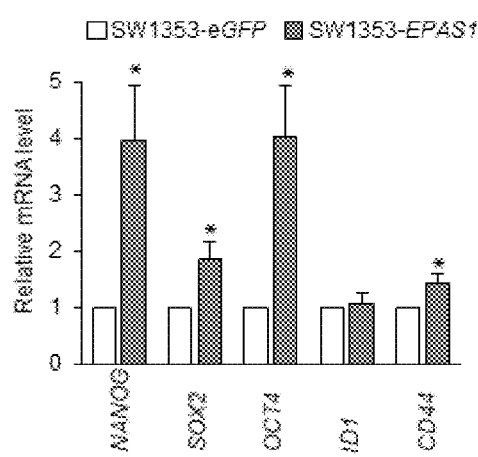
FIG. 4J shows the results of qRT-PCR analysis of pluripotency markers in SW1353 cells overexpressing eGFP or HIF-2α (n=7). (P=0.02 (NANOG), P=0.02 (SOX2), P=0.02 (OCT4), P=0.02 (CD44) n=7)
Figure 4K:
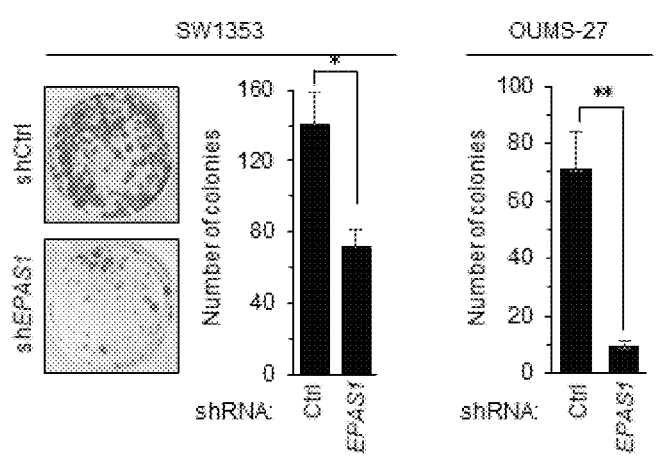
FIG. 4K shows the representative images and quantification of colony formation assay by SW1353 (Left, P=0.03, n=4) and OUMS-27 (P=0.01, Right, n=6) cells expressing indicated EPAS1 shRNAs or ctrl
Figure 4L:
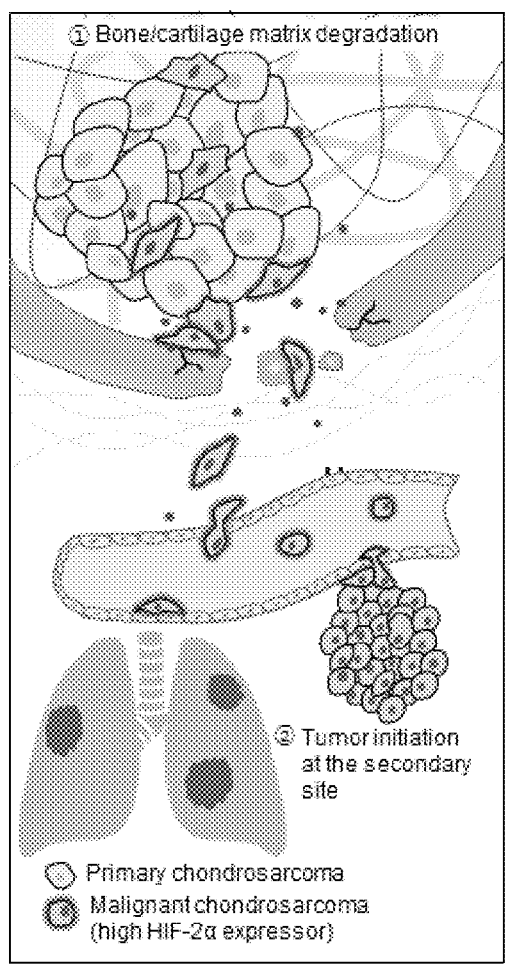
FIG. 4L shows schematic representation of the role of HIF-2α in potentiating chondrosarcoma metastasis.

Example 5: Identification that HIF-2α Expression Confers Tumor-Initiating Capacity to Chondrosarcoma To complete the metastatic process, cells disseminating from the primary tumor need to attain clonogenic and self-renewal properties to colonize secondary sites (Reya T, et al. Stem cells, cancer, and cancer stem cells. Nature. 2001; 414(6859):105-111). These tumor-initiating behaviors are often associated with the acquisition of cancer stemness (Wu C, et al. Side population cells isolated from mesenchymal neoplasms have tumor initiating potential. Cancer Res. 2007; 67(17):8216-8222). Thus, we explored whether HIF-2α drives this reprogramming in chondrosarcoma cells. In response to HIF-2α knockdown, SW1353 transcriptome was negatively enriched with 'cancer stem cell' genesets (FIG. 4F), suggesting a possible link between HIF-2α and cancer stemness. In sphere-forming assays to gauge cancer stemness, HIF-2α was upregulated in these sphere-forming SW1353 and OUMS-27 cells compared with those grown as a monolayer (FIG. 4G). A crosscheck with the public dataset (Desiderio V, et al. Molecular Profiling of Human Primary Chondrosarcoma-Derived Spheres Reveals Specific and Target Genes Involved in Multidrug Resistance and Metastasis. J Carcinogene Mutagene. 2013; 5(1)) showed that the HIF-2α level was consistently elevated in spheres of primary cultured chondrosarcoma cells in comparison to their monolayer counterparts (FIG. 4G). The sphere-forming potential of chondrosarcoma cell lines was significantly impaired by knockdown of HIF-2α (FIGS. 4H and 4I and FIG. 9, A). Indeed, HIF-2α regulated the transcription of major pluripotency genes including NANOG, SOX2, OCT4, and CD44, all of which possess HIF binding sites as predicted by TRANSFAC analysis (FIG. 4J and FIG. 9B). Consistently, HIF-2α knockdown suppressed clonogenic ability of chondrosarcoma cells (FIG. 4K). Together, HIF-2α regulates key cellular processes required for chondrosarcoma metastasis (FIG. 4L).

Figure 10A:
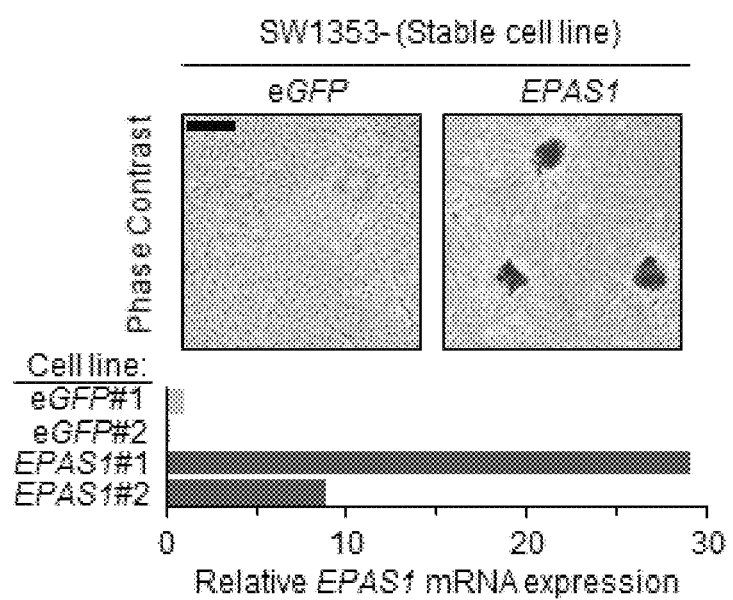
Figure 10B:
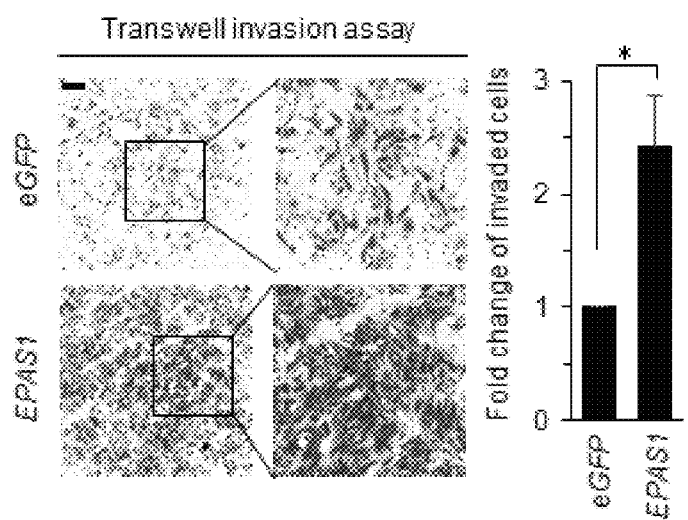
Figure 10C:
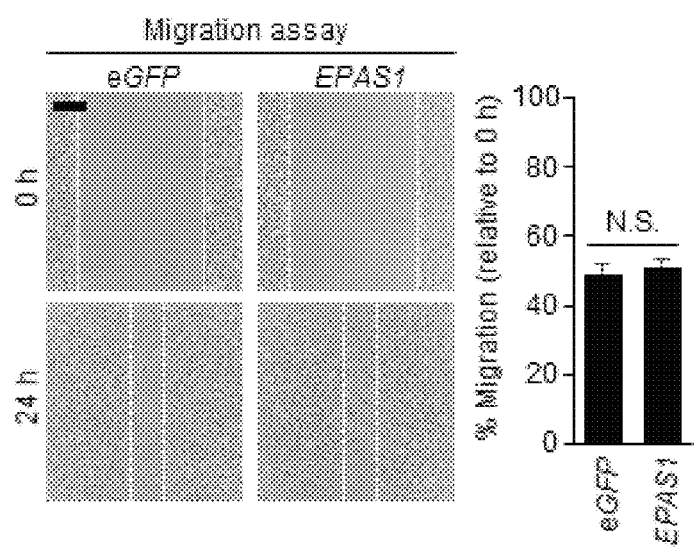
Figure 10D:
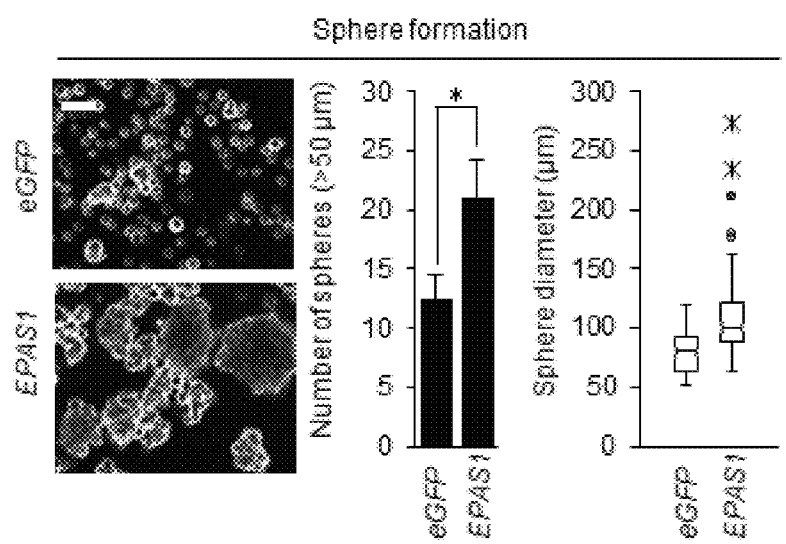
Figure 10E:
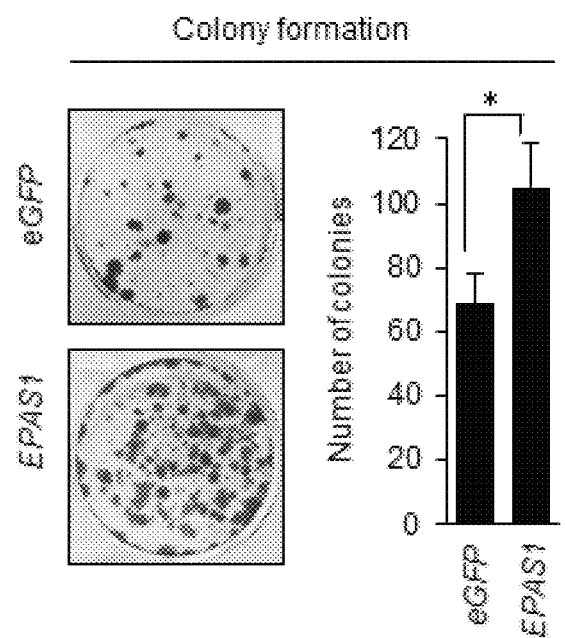
Figure 10F:
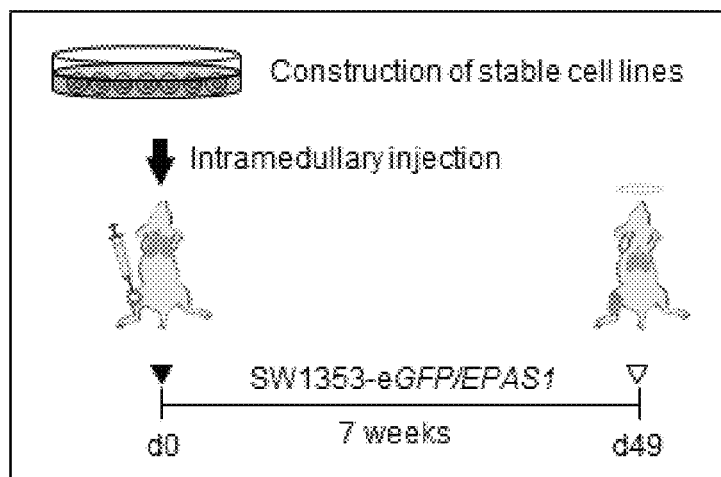
Figure 10G:
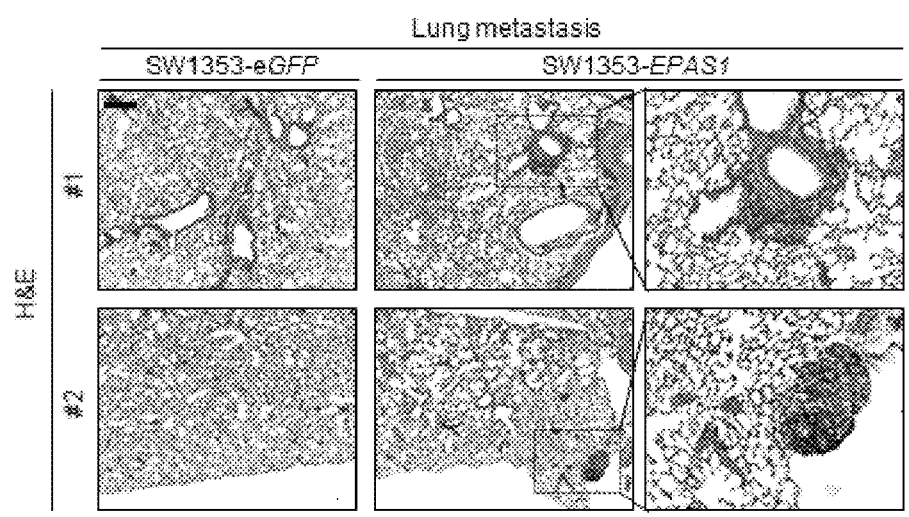
Figure 10H:
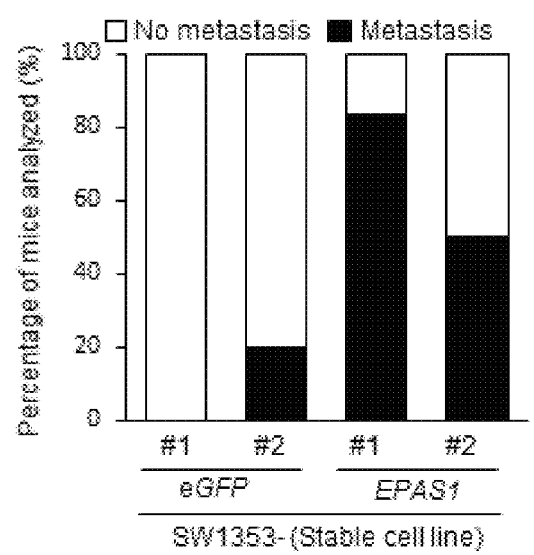
Figure 10I:
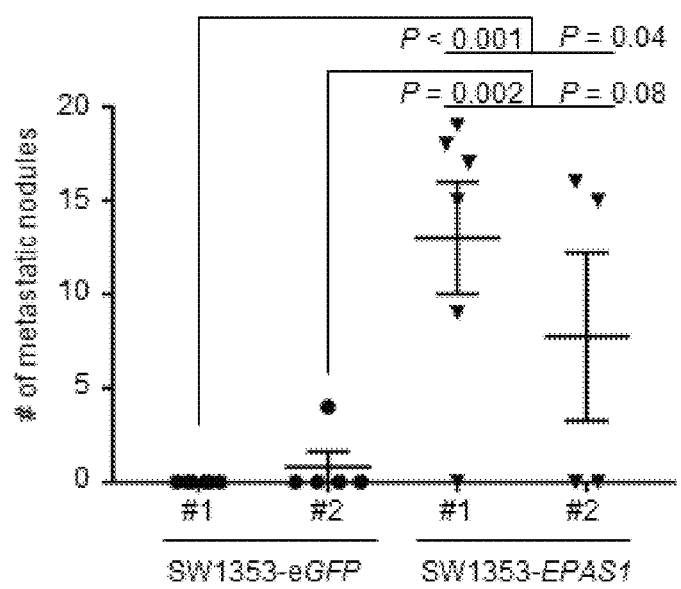

Example 6: Identification that HIF-2α-Overexpressing Chondrosarcoma Cells Acquire Enhanced Metastatic Potential To test whether HIF-2α plays a causal role in driving chondrosarcoma metastasis, we generated SW1353 cells stably overexpressing HIF-2α or eGFP. Notably, a subset of SW1353-EPAS1 stable cell lines spontaneously formed sarcospheres even in an adherent culture system (FIG. 10A). HIF-2α overexpression promoted invasiveness of SW1353 cells without affecting their migration rate (FIGS. 10B and 10C). HIF-2α overexpression enabled sphere formation even in the absence of growth factor supplements and markedly enhanced clonogenicity (FIGS. 10D and 10E). Next, HIF-2α- or eGFP-overexpressing cells were orthotopically implanted into athymic mice tibia (FIG. 10F). Mice injected with HIF-2α-overexpressing chondrosarcoma cells exhibited significantly increased metastasis (FIG. 10G-I), demonstrating a causal role of HIF-2α in driving metastasis of chondrosarcoma.

Figure 11A:
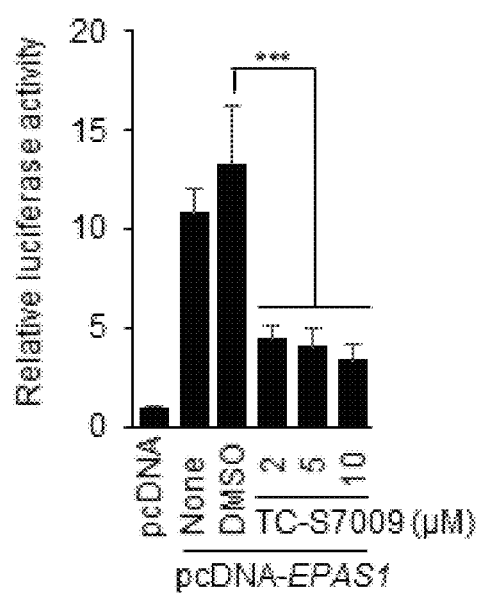
Figure 11B:
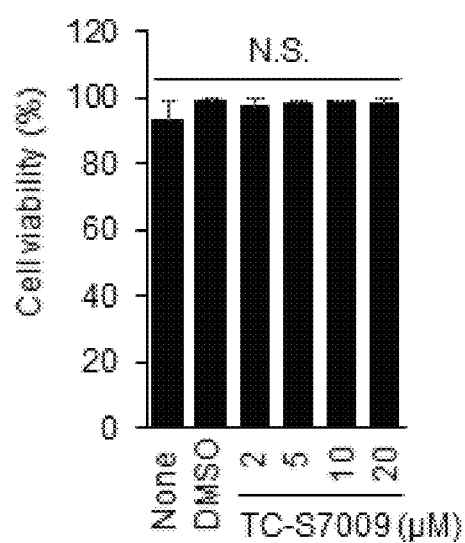
Figure 11C:
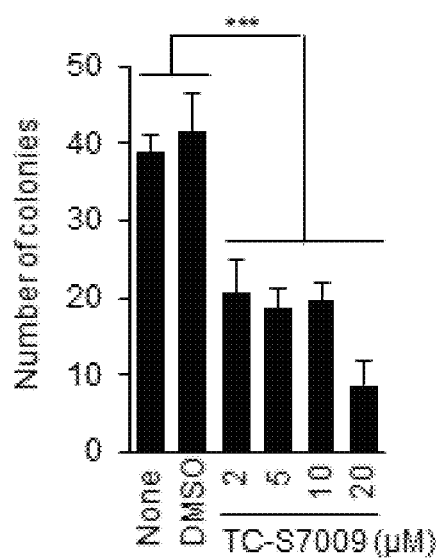
Figure 11D:
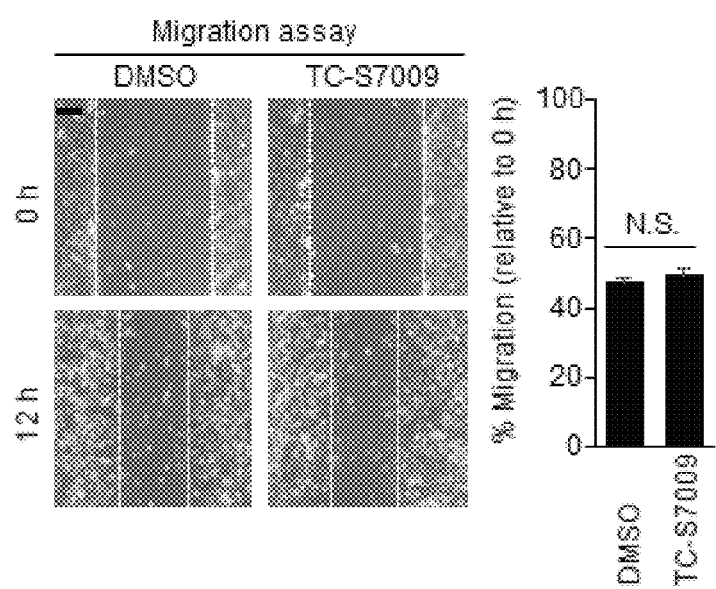

Example 7: Combined Treatment of HIF-2α Inhibitor and Cisplatin Effectively Blocks Chondrosarcoma Malignancy Chemoresistance is a major hurdle for clinical management of chondrosarcoma. Several molecular approaches targeting oncogenic signaling pathways mediated by EGFR (Song Y D, et al. Inhibition of EGFR-induced glucose metabolism sensitizes chondrosarcoma cells to cisplatin. Tumour Biol. 2014; 35(7):7017-7024), mTOR (Zhu Z, et al. MicroRNA-100 resensitizes resistant chondrosarcoma cells to cisplatin through direct targeting of mTOR. Asian Pac J Cancer Prev. 2014; 15(2):917-923), mTOR (Zhu Z, et al. MicroRNA-100 resensitizes resistant chondrosarcoma cells to cisplatin through direct targeting of mTOR. Asian Pac J Cancer Prev. 2014; 15(2):917-923), and Src (Huang K, et al. Inhibition of Src by microRNA-23b increases the cisplatin sensitivity of chondrosarcoma cells. Cancer Biomark. 2017; 18(3):231-239, Schrage Y M, et al. Kinome Profiling of Chondrosarcoma Reveals Src-Pathway Activity and Dasatinib as Option for Treatment. Cancer Res. 2009; 69(15): 6216-6222) have been successfully attempted to sensitize chondrosarcoma cells to anti-tumor agents such as cisplatin. We tested whether pharmacological inhibition of HIF-α activity may serve as a new option for adjuvant therapy for chondrosarcoma. A small molecule HIF-2α inhibitor, TC-S7009 (Scheuermann T H, et al. Allosteric inhibition of hypoxia inducible factor-2 with small molecules. Nat Chem Biol. 2013; 9(4):271-276), effectively abolished transcriptional activity of HIF-2α in chondrosarcoma cells without any apparent cytotoxicity (FIGS. 11A and 11B). TC-S7009 treatment effectively blocked invasive phenotypes, matrix-degrading activity, sphere formation, and clonogenicity in SW1353 cells (FIG. 5A to 5D and FIGS. 11C and 11D).

Our 'hallmark' pathway analysis indicated that HIF-2α knockdown caused positive enrichments of 'apoptosis' and 'p53 pathway' genesets (FIG. 3D), which are directly related to apoptotic pathways. However, TC-S7009 alone did not noticeably affect cell death (FIG. 5E). Cisplatin alone caused a mild increase in Annexin-V and propidium iodide (PI) positive populations (FIG. 5E), supporting the notion that chondrosarcoma cells are highly resistance to cisplatin. In contrast, combined treatment with TC-S7009 and cisplatin markedly elevated the fraction of Annexin-V positive cells (FIG. 5E), suggesting the synergistic role of the two agents in triggering apoptosis of chondrosarcoma cells.

To further explore the synergism between HIF-2α inhibition and cisplatin, we adopted the Chou-Talalay method to calculate the combination index (CI), which allows quantitative characterization of drug combinations (Chou T C. Drug Combination Studies and Their Synergy Quantification Using the Chou-Talalay Method. Cancer Res. 2010; 70(2):440-446). ABT-888, a PARP inhibitor, and Nutlin-3a, a p53 activator, were used as positive controls owing to their well-characterized effects on sensitizing cisplatin-induced apoptosis in various cancer cell types (Donawho C K, et al. ABT-888, an orallyactive poly(ADP-ribose) polymerase inhibitor that potentiates DNA-damaging agents in preclinical tumor models. Clin Cancer Res. 2007; 13(9):2728-2737, Deben C, et al. The MDM2-inhibitor Nutlin-3 synergizes with cisplatin to induce p53 dependent tumor cell apoptosis in non-small cell lung cancer. Oncotarget. 2015; 6(26): 22666-22679). The cisplatin-TC-S7009 and cisplatin-ABT-888 combinations exhibited stronger synergistic cell growth inhibition than the cisplatin-Nutlin-3a combination (FIG. 5F).

Potential in vivo therapeutic effects of a HIF-2α inhibitor as a chemotherapy adjuvant were assessed in tumor xenografts. Mice with established SW1353 tumors were treated with vehicle, cisplatin, TC-S7009, or cisplatin in combination with TC-S7009 (FIG. 5G). Cisplatin or TC-S7009 treatment alone caused a mild-to-moderate reduction in extraosseous outgrowth and pulmonary metastatic nodule formation (FIGS. 5 I, K, and L). Interestingly, in mice that received the combined therapy of cisplatin and TC-S7009, invasive outgrowth of primary tumor at the bone surface was nearly abolished and a profound effect on lung metastasis suppression was observed (FIG. 5 H-L).

Example 8: Identification of Association Between HIF-2α Pathway Alterations and Cancer Prognosis in Patients with Chondrosarcoma We questioned whether there are potential associations of CNAs (copy number alteration) affecting the HIF-2α pathway with the prognosis of patients with chondrosarcoma. Genomic profiles of 67 patients indicated significant genomic instability of varying degrees (Hallor K H, et al. Genomic profiling of chondrosarcoma: chromosomal patterns in central and peripheral tumors. Clin Cancer Res. 2009; 15(8):2685-2694). We analyzed CNAs in HIF1A and EPAS1 loci using the Gain and Loss Analysis of DNA (GLAD) segmentation method (FIG. 6A and FIG. 12) (Hupe P, et al. Analysis of array CGH data: from signal ratio to gain and loss of DNA regions. Bioinformatics. 2004; 20(18): 3413-3422). The CNAs in HIF1A locus had no significant effect on either overall or recurrence-free survival (FIG. 6B). In contrast, patients with copy number gain of EPAS1 locus exhibited poorer prognosis in comparison to patients with a loss or no alteration of EPAS1 copy number (FIG. 6C). We then focused on the CNA status of the von Hippel-Lindau tumor suppressor protein (pVHL), which is the recognition component of the E3-ubiquitin ligase complex degrading HIF proteins. In fact, loss of VHL was associated with increased HIF-2α activity in chondrocytes (Weng T, et al. Loss of Vhl in cartilage accelerated the progression of age-associated and surgically induced murine osteoarthritis. Osteoarthr Cartilage. 2014; 22(8):1197-1205). We classified 67 patients with chondrosarcoma into two groups according to the CNA status of EPAS1 and VHL such that group 1 was postulated to have a hyperactive HIF-2α pathway and group 2 a comparatively lower activity (FIG. 6D). Accordingly, group 1 patients exhibited substantially poorer prognosis than group 2 patients in terms of both overall and recurrence-free survival, suggesting the practicality of a screen for "high risk" among patients with chondrosarcoma based on genomic alterations in HIF-2α pathway components (FIG. 6E).

Chondrosarcoma ranges from low-grade tumors with virtually no metastatic potential to high-grade or dedifferentiated, aggressive tumors characterized by metastatic spread and recurrence, which become treatment-refractory and lead to a poor prognosis.

We inspected the system-level properties of whole transcriptomes of patients with chondrosarcoma. Gene co-expression analysis often provides a useful global perspective on perturbed transcriptional networks in cancer. This system-wide transcriptome analysis can be further used to construct a roadmap toward the identification of key therapeutic targets for diseases. By conducting WGCNA in patient transcriptomes, we extracted a characteristic gene module potentially responsible for chondrosarcoma malignancy and identified HIF-2α as a master regulator of the module.

A positive correlation between HIF-2α levels and histological grades of chondrosarcoma in patients was noted previously (Chen C, et al. Association of elevated HIF-2alpha levels with low Beclin 1 expression and poor prognosis in patients with chondrosarcoma. Ann Surg Oncol. 2011; 18(8):2364-2372). In this study, we observed that HIF-2α expression is more significantly associated with dedifferentiated than well-differentiated chondrosarcoma. We also demonstrate that HIF-2α plays a central role in the transition of chondrosarcomas to a highly metastatic and treatment-refractory state. HIF-2α endowed chondrosarcoma cells with a high propensity for osteolytic invasion by inducing the expression of MMP1, MMP2, and MMP9, which are of particular importance in destructing the bone matrix and enhancing invasiveness. These findings are in line with the increased expression of these proteins in metastatic chondrosarcomas (Soderstrom M, et al. Expression of matrix metalloproteinases and tissue inhibitors of metalloproteinases in human chondrosarcomas. APMIS. 2001; 109(4):305-315, Schoedel K E, et al. Expression of metalloproteinases and tissue inhibitor in cartilaginous neoplasms of bone. Appl Immunohistochem. 1997; 5(2):111-116). Moreover, our results indicate that HIF-2α promotes tumor initiation at metastatic sites by conferring chondrosarcoma cells self-renewal and clonogenic abilities.

Several pathological and cellular features of chondrosarcomas, such as their low proliferation rate, have limited the efficacy of conventional anti-cancer therapies. We showed that HIF-2α inhibition in conjunction with a conventional chemotherapy agent effectively alleviates chondrosarcoma malignancy through their synergistic effects on triggering chondrosarcoma cell apoptosis. Two recently developed HIF-2α antagonists, functional analogues of TC-S7009, demonstrated potential clinical use in clear cell renal cell carcinoma possessing elevated HIF-2α levels (Chen W, et al. Targeting renal cell carcinoma with a HIF-2 antagonist. Nature. 2016; 539(7627):112-117, Cho H, et al. On-target efficacy of a HIF-2alpha antagonist in preclinical kidney cancer models. Nature. 2016; 539(7627):107-111.) our findings suggest that HIF-2α can be a potential druggable target and an intriguing possibility of developing therapeutic strategies for chondrosarcoma patients with HIF-2α hyperactivity.

TABLE 1

List of clustered patients and clinicopathological features, referring to FIG. 1H

|  | Case number | Grade | 5-year overall survival | Dedifferentiation |
|---|---|---|---|---|
| group1 | case_2 | 3 |  | ● |
|  | case_4 | 2 | ● | ● |
|  | case_29 | 3 |  | ● |
|  | case_37 | 3 |  | ● |
|  | case_38 | 2 |  |  |
|  | case_50 | 1 | ● |  |
| group2 | case_11 | 2 | ● |  |
|  | case_14 | 2 | ● |  |
|  | case_15 | 3 |  |  |
|  | case_20 | 2 | ● |  |
|  | case_26 | 2 | ● |  |
|  | case_28 | 2 | ● |  |
|  | case_34 | 2 | ● |  |
|  | case_55 | 2 | ● |  |
|  | case_63 | 2 | ● |  |

TABLE 2-1

List of siRNA sequences used in this study
siRNA sequences

| Name | Sequence (5'→3') | SEQ ID NO. |
|---|---|---|
| HIF1A siRNA - sense | GUGGUUGGAUCUAACACUA(dT dT) | SEQ ID NO: 1 |
| HIF1A siRNA - antisense | UAGUGUUAGAUCCAACCAC(dT dT) | SEQ ID NO: 2 |
| HIF-2α (EPAS1) siRNA - sense | ACUACGUCCUGAGUGAGAU(dT dT) | SEQ ID NO: 3 |
| HIF-2α (EPAS1) siRNA - antisense | AUCUCACUCAGGACGUAGU(dT dT) | SEQ ID NO: 4 |

TABLE 2-2

List of shRNA cloning primers used in this study
shRNA cloning primers

| Name | Sequence (5'→3') | SEQ ID NO. |
|---|---|---|
| scramble shRNA pLKO.1-F (control) | CCGGAAACAAGATGAAGAGCACCAACT CGAGTTGGTGCTCTTCATCTTGTTTTT TTTG | SEQ ID NO: 5 |
| scramble shRNA pLKO.1-R (control) | AATTCAAAAAAACAAGATGAAGAGCA CCAACTCGAGTTGGTGCTCTTCATCTT GTTT | SEQ ID NO: 6 |
| HIF-2α (EPASI) shRNA oligo pLKO.1-F | CCGGCAGTACCCAGACGGATTTCAACT CGAGTTGAAATCCGTCTGGGTACTGTT TTTG | SEQ ID NO: 7 |
| HIF-2α (EPASI) shRNA oligo pLKO.1-R | AATTCAAAAACAGTACCCAGACGGATT TCAACTCGAGTTGAAATCCGTCTGGGT ACTG | SEQ ID NO: 8 |

TABLE 2-3

List of quantitative RT-PCR primers used in this study
Quantitative RT-PCR primers

| Name | Sequence (5'→3') | SEQ ID NO. |
|---|---|---|
| HIF-2α (EPAS1)-F | GAGCAAGGAGACGGAGGTGTT | SEQ ID NO: 9 |
| HIF-2α (EPAS1)-R | ATTGTGAGGAGGGCAGTTGTTG | SEQ ID NO: 10 |
| HPRT-F | CCTGGCGTCGTGATTAGTG | SEQ ID NO: 11 |
| HPRT-R | CTTGCGACCTTGACCATCTTT | SEQ ID NO: 12 |
| OCT4-F | ACAACGAGAGGATTTTGAGGCT | SEQ ID NO: 13 |
| OCT4-R | AGAGTGGTGACGGAGACAGG | SEQ ID NO: 14 |
| NANOG-F | CCTATGCCTGTGATTTGTGGG | SEQ ID NO: 15 |
| NANOG-R | GGGTTGTTTGCCTTTGGGAC | SEQ ID NO: 16 |
| SOX2-F | ATGGGTTCGGTGGTCAAGTCC | SEQ ID NO: 17 |
| SOX2-R | ATGTGTGAGAGGGGCAGTGTG | SEQ ID NO: 18 |
| ID1-F | TGCTGCTCTACGACATGAACG | SEQ ID NO: 19 |
| ID1-R | GCTCCAACTGAAGGTCCCTGA | SEQ ID NO: 20 |
| MMP1-F | TGAAGGTGATGAAGCAGCCC | SEQ ID NO: 21 |
| MMP1-R | TCCTGTAGGTCAGATGTGTTTG | SEQ ID NO: 22 |
| MMP2-F | CAAGTCTGGAGCGATGTGACC | SEQ ID NO: 23 |
| MMP2-R | CCTGGAAGCGGAATGGAAACT | SEQ ID NO: 24 |
| MMP9-F | CGCTATGGTTACACTCGGG | SEQ ID NO: 25 |
| MMP9-R | TAGGTGATGTTGTGGTGGTG | SEQ ID NO: 26 |
| HIF1A-F | TGTCTCCATTACCCACCGCT | SEQ ID NO: 27 |
| HIF1A-R | ACTGTGCTTTGAGGACTTGCG | SEQ ID NO: 28 |
| VEGFA-F | GGCAGAATCATCACGAAGTGG | SEQ ID NO: 29 |
| VEGFA-R | GAAGCTCATCTCTCCTATGTGC | SEQ ID NO: 30 |

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

What is claimed is:

1. A method of treating chondrosarcoma or suppressing metastasis or recurrence thereof in a subject in need thereof, the method comprising administering to the subject an effective amount of TC-S7009 [N-(3-Chloro-5-fluorophenyl)-4-nitro-2,1,3-benzoxadiazol-5-amine] and cisplatin,
   wherein the subject is a human; and
   the TC-S7009 inhibits transcriptional activity of HIF-2α.

2. The method of claim 1, wherein the chondrosarcoma is a dedifferentiated chondrosarcoma.

\* \* \* \* \*

SEQUENCE LISTING

<160> NUMBER OF SEQ ID NOS: 30

<210> SEQ ID NO 1
<211> LENGTH: 23
<212> TYPE: RNA
<213> ORGANISM: Artificial Sequence
<220> FEATURE:
<223> OTHER INFORMATION: siRNA_HIF1A siRNA - sense

<400> SEQUENCE: 1
gugguuggau cuaacacuad tdt                                          23

<210> SEQ ID NO 2
<211> LENGTH: 23
<212> TYPE: RNA
<213> ORGANISM: Artificial Sequence
<220> FEATURE:
<223> OTHER INFORMATION: siRNA_HIF1A siRNA - antisense

<400> SEQUENCE: 2
uaguguuaga uccaaccacd tdt                                          23

<210> SEQ ID NO 3
<211> LENGTH: 23
<212> TYPE: RNA
<213> ORGANISM: Artificial Sequence
<220> FEATURE:
<223> OTHER INFORMATION: siRNA_EPAS1 siRNA - sense

<400> SEQUENCE: 3
acuacguccu gagugagaud tdt                                          23

<210> SEQ ID NO 4
<211> LENGTH: 23
<212> TYPE: RNA
<213> ORGANISM: Artificial Sequence
<220> FEATURE:
<223> OTHER INFORMATION: siRNA_EPAS1 siRNA - antisense

<400> SEQUENCE: 4
aucucacuca ggacguagud tdt                                          23

<210> SEQ ID NO 5
<211> LENGTH: 58
<212> TYPE: DNA
<213> ORGANISM: Artificial Sequence
<220> FEATURE:
<223> OTHER INFORMATION: shRNA cloning primers_scramble shRNA pLKO.1-F
      (control)

<400> SEQUENCE: 5
ccggaaacaa gatgaagagc accaactcga gttggtgctc ttcatcttgt tttttttg    58

<210> SEQ ID NO 6
<211> LENGTH: 58
<212> TYPE: DNA
<213> ORGANISM: Artificial Sequence
<220> FEATURE:
<223> OTHER INFORMATION: shRNA cloning primers_scramble shRNA pLKO.1-R
      (control)

<400> SEQUENCE: 6
aattcaaaaa aaacaagatg aagagcacca actcgagttg gtgctcttca tcttgttt    58

<210> SEQ ID NO 7
<211> LENGTH: 58

```
<212> TYPE: DNA
<213> ORGANISM: Artificial Sequence
<220> FEATURE:
<223> OTHER INFORMATION: shRNA cloning primers_EPAS1 shRNA oligo
      pLKO.1-F

<400> SEQUENCE: 7
ccggcagtac ccagacggat ttcaactcga gttgaaatcc gtctgggtac tgttttttg       58

<210> SEQ ID NO 8
<211> LENGTH: 58
<212> TYPE: DNA
<213> ORGANISM: Artificial Sequence
<220> FEATURE:
<223> OTHER INFORMATION: shRNA cloning primers_EPAS1 shRNA oligo
      pLKO.1-R

<400> SEQUENCE: 8
aattcaaaaa cagtacccag acggatttca actcgagttg aaatccgtct gggtactg       58

<210> SEQ ID NO 9
<211> LENGTH: 21
<212> TYPE: DNA
<213> ORGANISM: Artificial Sequence
<220> FEATURE:
<223> OTHER INFORMATION: Quantitative RT-PCR primers_EPAS1-F

<400> SEQUENCE: 9
gagcaaggag acggaggtgt t                                              21

<210> SEQ ID NO 10
<211> LENGTH: 21
<212> TYPE: DNA
<213> ORGANISM: Artificial Sequence
<220> FEATURE:
<223> OTHER INFORMATION: Quantitative RT-PCR primers_EPAS1-R

<400> SEQUENCE: 10
gagcaaggag acggaggtgt t                                              21

<210> SEQ ID NO 11
<211> LENGTH: 19
<212> TYPE: DNA
<213> ORGANISM: Artificial Sequence
<220> FEATURE:
<223> OTHER INFORMATION: Quantitative RT-PCR primers_HPRT-F

<400> SEQUENCE: 11
cctggcgtcg tgattagtg                                                 19

<210> SEQ ID NO 12
<211> LENGTH: 21
<212> TYPE: DNA
<213> ORGANISM: Artificial Sequence
<220> FEATURE:
<223> OTHER INFORMATION: Quantitative RT-PCR primers_HPRT-R

<400> SEQUENCE: 12
cttgcgacct tgaccatctt t                                              21

<210> SEQ ID NO 13
<211> LENGTH: 22
<212> TYPE: DNA
<213> ORGANISM: Artificial Sequence
<220> FEATURE:
<223> OTHER INFORMATION: Quantitative RT-PCR primers_OCT4-F
```

<400> SEQUENCE: 13
acaacgagag gattttgagg ct                                              22

<210> SEQ ID NO 14
<211> LENGTH: 20
<212> TYPE: DNA
<213> ORGANISM: Artificial Sequence
<220> FEATURE:
<223> OTHER INFORMATION: Quantitative RT-PCR primers_OCT4-R

<400> SEQUENCE: 14
agagtggtga cggagacagg                                                 20

<210> SEQ ID NO 15
<211> LENGTH: 21
<212> TYPE: DNA
<213> ORGANISM: Artificial Sequence
<220> FEATURE:
<223> OTHER INFORMATION: Quantitative RT-PCR primers_NANOG-F

<400> SEQUENCE: 15
cctatgcctg tgatttgtgg g                                               21

<210> SEQ ID NO 16
<211> LENGTH: 20
<212> TYPE: DNA
<213> ORGANISM: Artificial Sequence
<220> FEATURE:
<223> OTHER INFORMATION: Quantitative RT-PCR primers_NANOG-R

<400> SEQUENCE: 16
gggttgtttg cctttgggac                                                 20

<210> SEQ ID NO 17
<211> LENGTH: 21
<212> TYPE: DNA
<213> ORGANISM: Artificial Sequence
<220> FEATURE:
<223> OTHER INFORMATION: Quantitative RT-PCR primers_SOX2-F

<400> SEQUENCE: 17
atgggttcgg tggtcaagtc c                                               21

<210> SEQ ID NO 18
<211> LENGTH: 21
<212> TYPE: DNA
<213> ORGANISM: Artificial Sequence
<220> FEATURE:
<223> OTHER INFORMATION: Quantitative RT-PCR primers_SOX2-R

<400> SEQUENCE: 18
atgtgtgaga ggggcagtgt g                                               21

<210> SEQ ID NO 19
<211> LENGTH: 21
<212> TYPE: DNA
<213> ORGANISM: Artificial Sequence
<220> FEATURE:
<223> OTHER INFORMATION: Quantitative RT-PCR primers_ID1-F

<400> SEQUENCE: 19
tgctgctcta cgacatgaac g                                               21

<210> SEQ ID NO 20
<211> LENGTH: 21

```
<212> TYPE: DNA
<213> ORGANISM: Artificial Sequence
<220> FEATURE:
<223> OTHER INFORMATION: Quantitative RT-PCR primers_ID1-R

<400> SEQUENCE: 20
gctccaactg aaggtccctg a                                        21

<210> SEQ ID NO 21
<211> LENGTH: 20
<212> TYPE: DNA
<213> ORGANISM: Artificial Sequence
<220> FEATURE:
<223> OTHER INFORMATION: Quantitative RT-PCR primers_MMP1-F

<400> SEQUENCE: 21
tgaaggtgat gaagcagccc                                          20

<210> SEQ ID NO 22
<211> LENGTH: 22
<212> TYPE: DNA
<213> ORGANISM: Artificial Sequence
<220> FEATURE:
<223> OTHER INFORMATION: Quantitative RT-PCR primers_MMP1-R

<400> SEQUENCE: 22
tcctgtaggt cagatgtgtt tg                                       22

<210> SEQ ID NO 23
<211> LENGTH: 21
<212> TYPE: DNA
<213> ORGANISM: Artificial Sequence
<220> FEATURE:
<223> OTHER INFORMATION: Quantitative RT-PCR primers_MMP2-F

<400> SEQUENCE: 23
caagtctgga gcgatgtgac c                                        21

<210> SEQ ID NO 24
<211> LENGTH: 21
<212> TYPE: DNA
<213> ORGANISM: Artificial Sequence
<220> FEATURE:
<223> OTHER INFORMATION: Quantitative RT-PCR primers_MMP2-R

<400> SEQUENCE: 24
cctggaagcg gaatggaaac t                                        21

<210> SEQ ID NO 25
<211> LENGTH: 19
<212> TYPE: DNA
<213> ORGANISM: Artificial Sequence
<220> FEATURE:
<223> OTHER INFORMATION: Quantitative RT-PCR primers_MMP9-F

<400> SEQUENCE: 25
cgctatggtt acactcggg                                           19

<210> SEQ ID NO 26
<211> LENGTH: 20
<212> TYPE: DNA
<213> ORGANISM: Artificial Sequence
<220> FEATURE:
<223> OTHER INFORMATION: Quantitative RT-PCR primers_MMP9-R

<400> SEQUENCE: 26
```
taggtgatgt tgtggtggtg                                                        20

<210> SEQ ID NO 27
<211> LENGTH: 20
<212> TYPE: DNA
<213> ORGANISM: Artificial Sequence
<220> FEATURE:
<223> OTHER INFORMATION: Quantitative RT-PCR primers_HIF1A-F

<400> SEQUENCE: 27
tgtctccatt acccaccgct                                                        20

<210> SEQ ID NO 28
<211> LENGTH: 21
<212> TYPE: DNA
<213> ORGANISM: Artificial Sequence
<220> FEATURE:
<223> OTHER INFORMATION: Quantitative RT-PCR primers_HIF1A-R

<400> SEQUENCE: 28
actgtgcttt gaggacttgc g                                                      21

<210> SEQ ID NO 29
<211> LENGTH: 21
<212> TYPE: DNA
<213> ORGANISM: Artificial Sequence
<220> FEATURE:
<223> OTHER INFORMATION: Quantitative RT-PCR primers_VEGFA-F

<400> SEQUENCE: 29
ggcagaatca tcacgaagtg g                                                      21

<210> SEQ ID NO 30
<211> LENGTH: 22
<212> TYPE: DNA
<213> ORGANISM: Artificial Sequence
<220> FEATURE:
<223> OTHER INFORMATION: Quantitative RT-PCR primers_VEGFA-R

<400> SEQUENCE: 30
gaagctcatc tctcctatgt gc                                                     22